United States Patent
Lee et al.

(10) Patent No.: US 8,940,936 B2
(45) Date of Patent: Jan. 27, 2015

(54) ARYLOXY PHENOXY ACRYLIC COMPOUND HAVING HIF-1 INHIBITION ACTIVITY, METHOD FOR PREPARING SAME, AND PHARMACEUTICAL COMPOSITION CONTAINING SAME AS AN ACTIVE INGREDIENT

(75) Inventors: Kyeong Lee, Seoul (KR); Mi Sun Won, Daejeon (KR); Hwan Mook Kim, Daejeon (KR); Song Kyu Park, Daejeon (KR); Kiho Lee, Daejeon (KR); Ki Hoon Lee, Daejeon (KR); Chang Woo Lee, Daejeon (KR); Jung Joon Lee, Daejeon (KR); Kyung Sook Chung, Daejeon (KR); Bo Kyung Kim, Daejeon (KR); Yinglan Jin, Seoul (KR); Seung-hee Lee, Daejeon (KR)

(73) Assignees: Korea Research Institute of Bioscience and Biotechnology, Daejeon (KR); Dongguk University Industry-Academic Cooperation Foundation, Seoul (KR)

( * ) Notice: Subject to any disclaimer, the term of this patent is extended or adjusted under 35 U.S.C. 154(b) by 4 days.

(21) Appl. No.: 13/880,642

(22) PCT Filed: Oct. 17, 2011

(86) PCT No.: PCT/KR2011/007710
§ 371 (c)(1),
(2), (4) Date: May 23, 2013

(87) PCT Pub. No.: WO2012/053787
PCT Pub. Date: Apr. 26, 2012

(65) Prior Publication Data
US 2013/0237542 A1 Sep. 12, 2013

(30) Foreign Application Priority Data

Oct. 20, 2010 (KR) .................. 10-2010-0102661

(51) Int. Cl.
*C07C 233/07* (2006.01)
*A61K 31/167* (2006.01)
*C07C 235/28* (2006.01)
*C07C 311/16* (2006.01)
*C07D 295/088* (2006.01)

(52) U.S. Cl.
CPC ............ *C07C 235/28* (2013.01); *C07C 233/07* (2013.01); *A61K 31/167* (2013.01); *C07C 311/16* (2013.01); *C07D 295/088* (2013.01)
USPC .......................................... 564/175; 514/622

(58) Field of Classification Search
CPC ........................... C07C 233/07; A61K 31/167
USPC .......................................... 564/175; 514/622
See application file for complete search history.

(56) References Cited

U.S. PATENT DOCUMENTS

2008/0004323 A1 1/2008 Itoh et al.

OTHER PUBLICATIONS

Joo Eun Jung et al; Caffeic Acid and Its Synthetic Derivative Cadpe Suppress Tumor Angiogenesis by Blocking Stat3-Mediated VEGF Expression in Human Renal Carcinoma Cells; Carcinogenesis vol. 28, No. 8, pp. 1780-1787; 2007.
Uffe Hogh Olesen et al; Anticancer Agent CHS-828 Inhibits Cellular Synthesis of NAD; Biochemical and Biophysical Research Communications 367; pp. 799-804; 2008.

*Primary Examiner* — Robert Havlin
(74) *Attorney, Agent, or Firm* — Lucas & Mercanti, LLP

(57) ABSTRACT

The present invention relates to a compound inhibiting HF-1 activity, a preparation method of the same, and a pharmaceutical composition comprising the same as an active ingredient. The compound of the present invention demonstrates anticancer activity not by non-selective cytotoxicity but by inhibiting the activity of HIF-1, the transcription factor playing an important role in cancer cell growth and metastasis. Accordingly, the compound or the pharmaceutically acceptable salt thereof according to the present invention inhibits HIF-1 activity, and therefore can be used as a therapeutic agent for solid tumors such as colon cancer, liver cancer, stomach cancer and breast cancer. In addition, the compound or the pharmaceutically acceptable salt thereof according to the present invention can be used as an active ingredient for a therapeutic agent for diabetic retinopathy or arthritis which may become worse when hypoxia-induced VEGF expression by HIF-1 increases.

19 Claims, 10 Drawing Sheets

Fig. 8
Control group
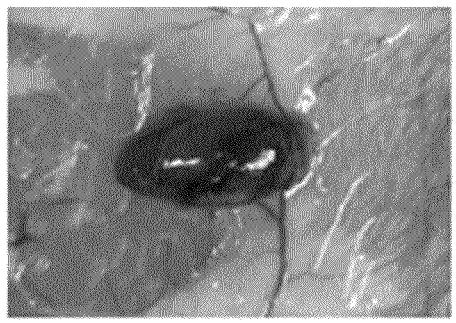 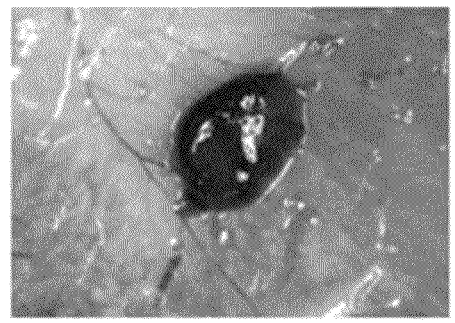
Experimental group
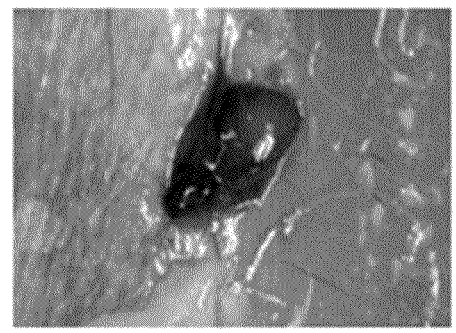 
Comparative group
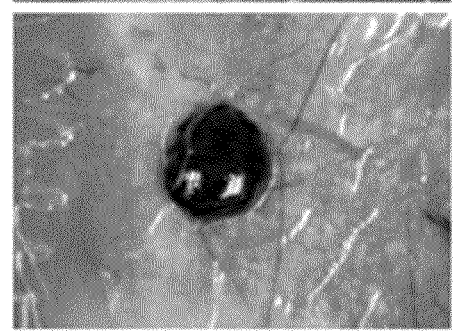 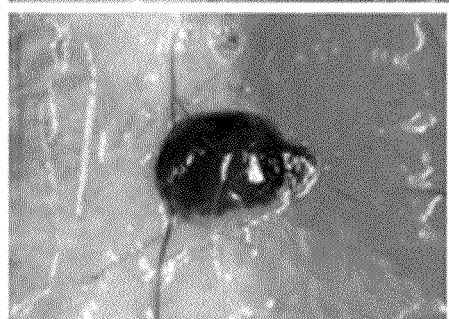

ARYLOXY PHENOXY ACRYLIC COMPOUND HAVING HIF-1 INHIBITION ACTIVITY, METHOD FOR PREPARING SAME, AND PHARMACEUTICAL COMPOSITION CONTAINING SAME AS AN ACTIVE INGREDIENT

CROSS-REFERENCES TO RELATED APPLICATION

This patent application is a 371 of PCT/KR2011/007710, filed on Oct. 17, 2011, which claims the benefit of Korean Patent Application No. 10-2010-0102661, filed on Oct. 20, 2010, the contents of each of which are incorporated herein by reference.

BACKGROUND OF THE INVENTION

1. Field of the Invention

The present invention relates to an aryloxy phenoxy acrylic compound having HIF-1 inhibition activity, a preparation method of the same, and a pharmaceutical composition containing the same as an active ingredient.

2. Description of the Related Art

Even after all the efforts over decades, cancer is still one of the most difficult untreatable diseases. Along with the striking advance in the fields of cancer cell biology, medicinal chemistry, etc, the development of a novel anticancer agent characteristically with a novel mechanism, such as Gleevec, has been made. Since Human Genome Project, novel target molecules has come to the front.

HIF-1 (Hypoxia Inducible Factor-1) is a transcription factor induced by hypoxia which is the heterodimer composed of HIF-1α subunit that is decomposed oxygen-dependently and HIF-1β subunit that is expressed all the time (Cancer Metastasis Rev., 17, 187-195, 1998; Trends Mol. Med., 7, 345-350, 2001). In the regular oxygen condition, the $402^{nd}$ and the $564^{th}$ proline residues of HIF-1α protein are hydroxylated, which are then combined with pVHL (Von Hippel-Lindau), the tumor suppressor gene, to be ubiquitinated that is later decomposed by proteasome. However, in hypoxia, a series of such reaction is inhibited, resulting in the accumulation of HIF-1α protein, which is combined with the existing HIF-1β protein. The conjugate migrates into the nucleus (Science 292, 468-472, 2001; Science 292, 468-472, 2001). The stability of HIF-1α is affected not only by oxygen partial pressure but also by other factors involved in oxygen sensing pathway which are exemplified by transition metal ions, iron chelators, and antioxidants, etc. HIF-1α can be accumulated regardless of oxygen concentration by the activation of such growth factors as epidermal growth factor, heregulin, insulin-like growth factors-I, and insulin-like growth factor-II, and oncogene such as ErβB2. When a growth factor is combined with each corresponding receptor, Pl3K-AKT, and MAPK signal transmission pathways are activated and HIF-1α protein synthesis is increased, resulting in the accumulation of HIF-1α protein.

HIF migrated into the nucleus is combined with HRE (Hypoxia Responsive Element, 5'-ACGTG-3') on the promoter of the target gene to induce the gene expression. Those genes regulated by HIF identified up to date are at least 60 genes including vascular endothelial growth factor A (VEGF) (*Nat. Rev. Cancer* 2, 38-47, 2002; *J. Biol. Chem.* 278, 19575-19578, 2003; *Nat, Med.* 9, 677-684, 2003; *Biochem. Pharmacol.* 64, 993-998, 2002).

Hypoxia is a general symptom of cancer, particularly of solid tumor. Solid tumor cells are well adapted to hypoxic condition after being through various genetic changes, indicating the cancer cells are more aggravated and malignant with demonstrating resistance against anticancer agents. In fact, hypoxia has been known to be the major reason of malignancy of at least 70% of all kinds of tumors found in human (Nature 386, 403, 1997; Hockel M and Vaupel P, Semin. Oncol. 28, 36-41, 2001, Nature Med. 6, 1335, 2000; Bos et al. Cancer 2003, 97, 1573-1581). HIF-1 has been known to be a major molecule that regulates the adaptation of cancer cells to hypoxic condition. So, it can be said that the concentration of HIF-1α protein closely relates to the prognosis of cancer patients. The activation of HIF-1 by the growth factor, the activation of oncogene, or the inactivation of tumor suppressor gene such as pVHL induces the expressions of such genes as hexokinase 2, glucose transporter 1, erythropoietin, IGF-2, endoglin, VEGF, MMP-2, uPAR, and MDR1, in hypoxic condition, resulting in the increase of resistance against apoptosis, the increase of angiogenesis, the increase of cell proliferation, and the increase of cell invasion, and hence in the malignant alteration of cancer cells. Since HIF plays an important role in the growth, proliferation, and malignant alteration of solid tumor, research for the development of an anticancer agent has been focused on HIF (Cancer Res. 62, 4316, 2002; Nat Rev Drug Discovery 2, 1, 2003; Semenza et al. Nature Reviews Cancer 2003, 3, 721-732). The conventional anticancer agents such as taxol, rafamycin, and 17-AAG (17-allylaminogeldanamycin) and the drug in the middle of clinical test such as the low molecular compound YC-1 (3-(5'-hydroxymethyl-2'-furyl)-1-benzylindazole)), which is a guanylaly cyclase activator, are all HIF-1 inhibitors (Johnson et al Nature Reviews Drug Discovery 2003, 2, 1-9; Semenza et al. Nature Reviews Cancer 2003, 3, 721-732; JNCI 95, 516, 2003). Studies to develop a HIF-1 inhibitor with a novel structure is also actively undergoing with cell based reporter assay using HRE (Cancer Res 65, 4918, 2005; Cancer Cell 6, 33, 2004; Cancer Res. 62, 4316, 2002).

HIF-1 is useful as a target of cancer and also of other diseases whose worsen relates to the activation of angiogenesis. Hypoxia-induced HIF-1 activation activates angiogenesis related factors such as VEGF, which plays a certain role in the progress of not only cancer but also diabetic retinopathy or arthritis. Therefore, the compound inhibiting HIF-1 activated by hypoxia in the disease tissue can be effectively used as a novel therapeutic agent for such disease as diabetic retinopathy or rheumatoid arthritis (Eiji Ikeda, Pathology International, 2005, Vol 55, 603-610). However, this field is in a very nascent stage.

Thus, the present inventors have studied about compounds being able to inhibit HIF-1 activity, during which the inventors synthesized a compound inhibiting HIF-1 activity, suppressing angiogenesis and cancer metastasis, but having enhanced stability in human body, leading to the completion of this invention.

SUMMARY OF THE INVENTION

It is an object of the present invention to provide a novel compound inhibiting HIF-1 activity.

It is another object of the present invention to provide a preparation method of the said novel compound.

It is another object of the present invention to provide a pharmaceutical composition for the treatment of cancer comprising the said novel compound as an active ingredient.

It is also an object of the present invention to provide a pharmaceutical composition for the treatment of diabetic retinopathy comprising the said novel compound as an active ingredient.

It is further an object of the present invention to provide a pharmaceutical composition for the treatment of rheumatoid arthritis comprising the said novel compound as an active ingredient.

To achieve the above objects, the present invention provides the compound represented by the following formula 1 or a pharmaceutically acceptable salt thereof:

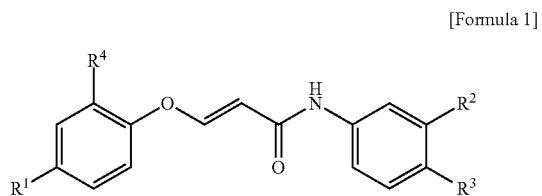

[Formula 1]

(In formula 1, $R^1$~$R^4$ are as defined in this description).

The present invention also provides a preparation method of the compound of formula 1, as shown in the following reaction formula 1, comprising the following step: Hunig base and condensation reagent are added to the compound represented by formula 2 and the compound represented by formula 3, used as the starting materials to induce reaction, in the presence of an organic solvent to give the compound represented by formula 1:

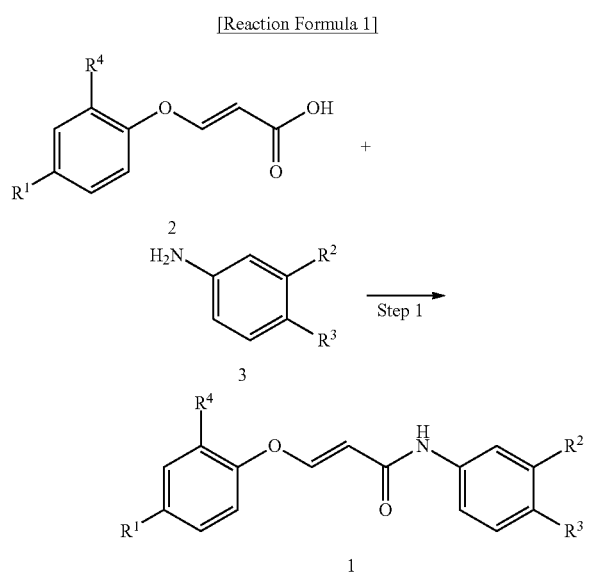

[Reaction Formula 1]

(In reaction formula 1, $R^1$~$R^4$ are as defined in this description).

The present invention also provides a pharmaceutical composition for the prevention or treatment of cancer comprising the compound represented by formula 1 or a pharmaceutically acceptable salt thereof as an active ingredient.

The present invention further provides a pharmaceutical composition for the prevention or treatment of diabetic retinopathy comprising the compound represented by formula 1 or a pharmaceutically acceptable salt thereof as an active ingredient.

In addition, the present invention provides a pharmaceutical composition for the prevention or treatment of rheumatoid arthritis comprising the compound represented by formula 1 or a pharmaceutically acceptable salt thereof as an active ingredient.

Advantageous Effect

As explained hereinbefore, the compound represented by formula 1 of the present invention shows anticancer activity not by non-selective cytotoxicity but by suppressing HRE transcription by inhibiting HIF-1 activity and further inhibiting VEGF and EPO expression specifically to suppress cancer growth and metastasis, so that it can be not only used as an active ingredient of an anticancer agent but also used as an active ingredient for a therapeutic agent for diabetic retinopathy or rheumatoid arthritis aggravated by VEGF expression.

BRIEF DESCRIPTION OF THE DRAWINGS

The application of the preferred embodiments of the present invention is best understood with reference to the accompanying drawings, wherein:

FIG. 8 is a photograph illustrating the effect of the compound of an example of the present invention on angiogenesis.

DESCRIPTION OF THE PREFERRED EMBODIMENTS

Figure 1:
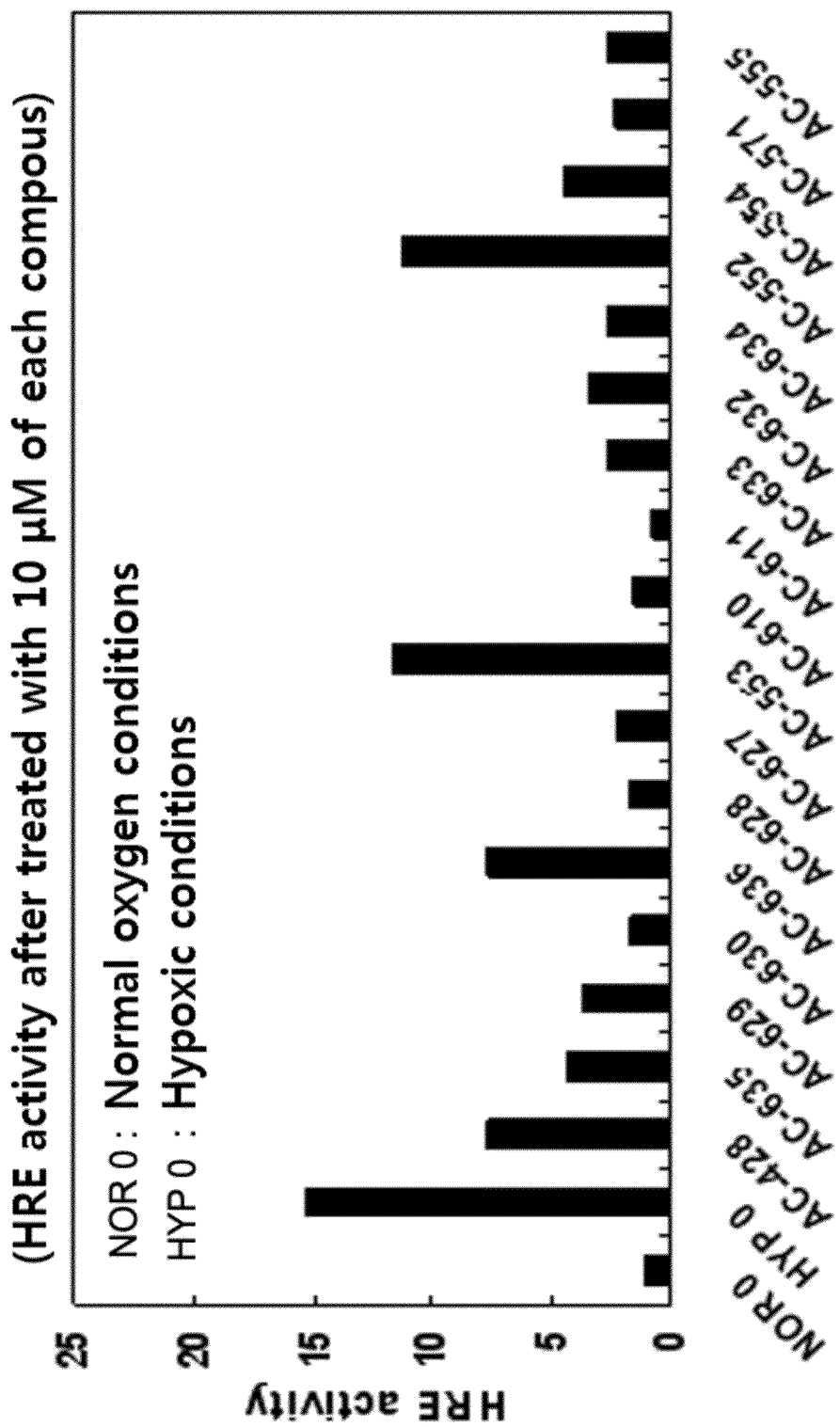
FIG. 1 is a graph illustrating the HRE transcription activity affected by the treatment of the compound of an example of the present invention at the concentration of 10 μM.

Hereinafter, the present invention is described in detail.

The present invention provides the novel aryloxyphenoxyacrylic compound represented by the following formula 1 or a pharmaceutically acceptable salt thereof.

[Formula 1]

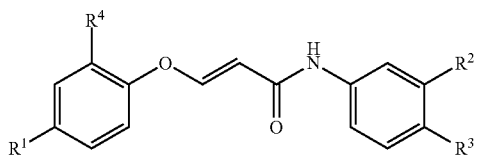

In the formula 1,

R¹ is $C_{1-10}$ straight or branched alkyl, or $C_{8-12}$ bicyclic ring,

R² is —H, COOR₅, COOR₅R₆, —SO₂NH₂, —SO₂—($C_{1-4}$ straight or branched alkyl), or —CONHR₇, R³ is —H, —OH, or —COO—($C_{1-4}$ straight or branched alkyl), R⁴ is —H, or $C_{1-4}$ straight or branched alkyl, R⁵ is —H, $C_{1-4}$ straight or branched alkyl, or $C_{1-4}$ alkoxy, R⁶ is —NH₂, or 5-6 membered heterocycle containing one or more N or O, R⁷ is —H, or —(CH₂)ₙ—R⁸, R⁸ is —H, 5-6 membered heteroaryl containing one or more N or O, or 5-6 membered heterocycle containing one or more N or O, and n is an integer of 0-4.

R¹ is $C_{1-10}$ straight or branched alkyl, or

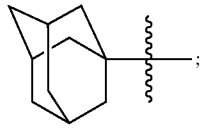 [SMILES: *C12CC3CC(CC(C3)C1)C2];

R² is —H, COOR₅, COOR₅R₆, —SO₂NH₂, —SO₂CH₃, or —CONHR₇;

R³ is —H, —OH, or COOCH₃;

R⁴ is —H, or methyl;

R⁵ is —H, methyl, ethyl, methoxy, or ethoxy;

R⁶ is —NH₂, or 5-6 membered heterocycle containing one or more N or O;

R⁷ is —H, or —(CH₂)ₙ—R⁸;

R⁸ is —H, 5-6 membered heteroaryl containing one or more N or O, or 6 membered heterocycle containing one or more N or O;

n is an integer of 0-3.

More preferably,

R¹ is

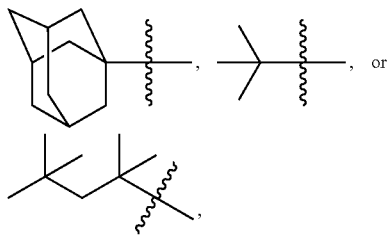

R² is —H, —COOH, —COOCH₃, —COOCH₂CH₃, —COOCH₂CH₂OCH₃, —CONH₂, —SO₂NH₂, —SO₂CH₃,

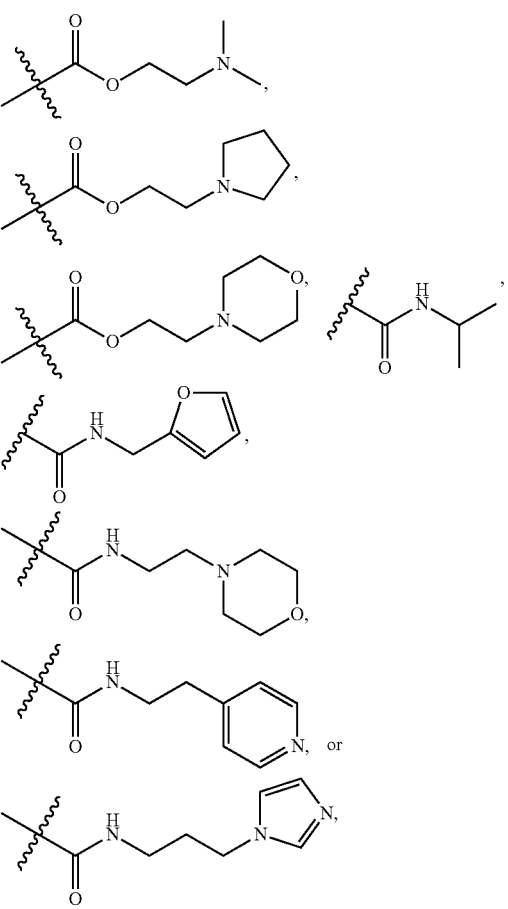

R³ is —H, —OH, or —COOCH₃, and

R⁴ is —H, or methyl.

The examples of the compound of formula 1 are as follows.

(1) (E)-3-[3-(4-adamantan-1-yl-phenoxy)-acryloylamino]-benzoic acid methylester, (2) (E)-3-(3-(4-t-butylphenoxy)acrylamido)benzoic acid methylester, (3) (E)-3-(3-(4-(2,4,4-trimethylpentan-2-yl)phenoxy)acrylamido)benzoic acid methylester, (4) (E)-3-(3-(4-adamantan-1-yl-2-methylphenoxy)acrylamido)benzoic acid methylester, (5) (E)-4-(3-(4-adamantan-1-ylphenoxy)acrylamido)benzoic acid methylester, (6) (E)-3-(4-adamantan-1-ylphenoxy)-N-(3-sulfamoylphenyl)acrylamide, (7) (E)-3-(4-adamantan-1-ylphenoxy)-N-(3-(methylsulfonyl)phenyl)acrylamide, (8) (E)-5-[3-(4-adamantan-1-yl-phenoxy)-acryloamino]-2-hydroxy-benzoic acid methylester, (9) (E)-3-[3-(4-adamantan-1-yl-phenoxy)-acryloylamino]-benzoic acid,

(10) (E)-3-(3-(4-adamantan-1-ylphenoxy)acrylamido)benzoic acid ethylester,

(11) (E)-3-(3-(4-adamantan-1-ylphenoxy)acrylamido)benzoic acid 2-methoxyethylester,

(12) (E)-3-(3-(4-adamantan-1-yl-phenoxy)acrylamido)benzoic acid 2-(dimethylamino)ethylester,

(13) (E)-3-(3-(4-adamantan-1-ylphenoxy)acrylamido)benzoic acid 2-pyrrolidine-1-yl)ethylester,

(14) (E)-3-(3-(4-adamantan-1-ylphenoxy)acrylamido)benzoic acid morpholinoethylester,

(15) (E)-3-[3-(4-adamantan-1-yl-phenoxy)-acryloylamino]-benzamide,
(16) (E)-3-[3-(4-adamantan-1-yl-phenoxy)-acryloylamino]-N-isopropyl-benzamide,
(17) (E)-3-[3-(4-adamantan-1-yl-phenoxy)-acryloylamino]-N-furan-2-ylmethyl-benzamide,
(18) (E)-3-[3-(4-adamantan-1-yl-phenoxy)-acryloylamino]-N-(2-morpholine-4-yl-ethyl)-benzamide,
(19) (E)-3-[3-(4-adamantan-1-yl-phenoxy)-acryloylamino]-N-(2-pyridine-4-yl-ethyl)-benzamide,
(20) (E)-3-[3-(4-adamantan-1-yl-phenoxy)-acryloylamino]-N-(3-imidazole-1-yl-propyl)-benzamide,
(21) (E)-3-(3-(4-(2,4,4-trimethylpentan-2-yl)phenoxy)acrylamido)benzoic acid,
(22) (E)-2-methoxyethyl 3-(3-(4-(2,4,4-trimethylpentan-2-yl)phenoxy)acrylamido)benzoate, and
(23) (E)-2-morpholinoethyl 3-(3-(4-(2,4,4-trimethylpentan-2-yl)phenoxy)acrylamido)benzoate.

The examples of the novel aryloxyphenoxyacrylic compound of formula 1 are described in Table 1.

TABLE 1

| Example No. | Structure R$^1$ | R$^2$ | R$^3$ | R$^4$ |
|---|---|---|---|---|
| Example 1 | 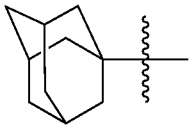 [SMILES: *C12CC3CC(CC(C3)C1)C2] | COOCH$_3$ | H | H |
| Example 2 | 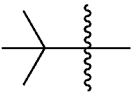 | COOCH$_3$ | H | H |
| Example 3 | 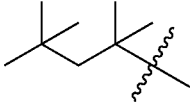 [SMILES: *C(C)(C)CC(C)(C)C] | COOCH$_3$ | H | H |
| Example 4 | 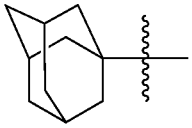 | COOCH$_3$ | H | CH$_3$ |
| Example 5 | 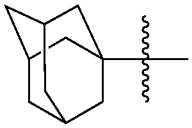 [SMILES: *C12CC3CC(CC(C3)C1)C2] | H | COOCH$_3$ | H |
| Example 6 | 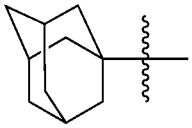 [SMILES: *C12CC3CC(CC(C3)C1)C2] | SO$_2$NH$_2$ | H | H |
| Example 7 | 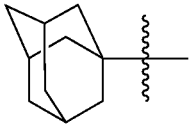 [SMILES: *C12CC3CC(CC(C3)C1)C2] | SO$_2$CH$_3$ | H | H |
| Example 8 | 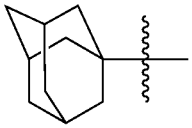 [SMILES: *C12CC3CC(CC(C3)C1)C2] | COOCH$_3$ | OH | H |

TABLE 1-continued

| Example No. | R¹ (Structure) | R² | R³ | R⁴ |
|---|---|---|---|---|
| Example 9 | adamantyl | COOH | H | H |
| Example 10 | adamantyl | COOCH₂CH₃ | H | H |
| Example 11 | adamantyl | COOCH₂CH₂OCH₃ | H | H |
| Example 12 | adamantyl | —C(=O)OCH₂CH₂N(CH₃)₂ | H | H |
| Example 13 | adamantyl | —C(=O)OCH₂CH₂-(pyrrolidin-1-yl) | H | H |
| Example 14 | adamantyl | —C(=O)OCH₂CH₂-(morpholin-4-yl) | H | H |
| Example 15 | adamantyl | CONH₂ | H | H |
| Example 16 | adamantyl | —C(=O)NH-iPr | H | H |
| Example 17 | adamantyl | —C(=O)NHCH₂-(furan-2-yl) | H | H |
| Example 18 | adamantyl | —C(=O)NHCH₂CH₂-(morpholin-4-yl) | H | H |
| Example 19 | adamantyl | —C(=O)NHCH₂CH₂-(pyridin-4-yl) | H | H |

The present invention not only includes the novel aryloxyphenoxyacrylic compound represented by formula 1 or a pharmaceutically acceptable salt thereof but also includes every possible solvates, hydrates, or prodrugs constructed from the same.

The compound represented by formula 1 of the present invention can be used as the form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, or phosphorous acid; or non-toxic organic acids such as aliphatic mono/di-carboxylate, phenyl-substituted alkanoate, hydroxy alkanoate/alkanedioate, aromatic acids, aliphatic and aromatic sulfonic acids. The pharmaceutically non-toxic salt is exemplified by sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, maliate, butin-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, or mandelate.

The acid addition salt in this invention can be prepared by the conventional method known to those in the art. For example, the compound of formula 1 is dissolved in excessive acid aqueous solution, followed by salt precipitation using water-miscible organic solvent such as methanol, ethanol, acetone, or acetonitrile. Equal amount of the compound of formula 1 and acid or alcohol in water are heated, followed by drying the mixture to give acid addition salt or suction-filtering the precipitated salt to give the same.

A pharmaceutically acceptable metal salt can be prepared by using base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention also provides a preparation method of the novel aryloxyphenoxyacrylic compound of formula 1.

The preparation method of the present invention contains the following step: As shown in the following reaction formula 1, Hunig base and condensation reagent are added to the compound represented by formula 2 and the compound represented by formula 3, used as the starting materials to induce reaction, in the presence of an organic solvent to give the compound represented by formula 1:

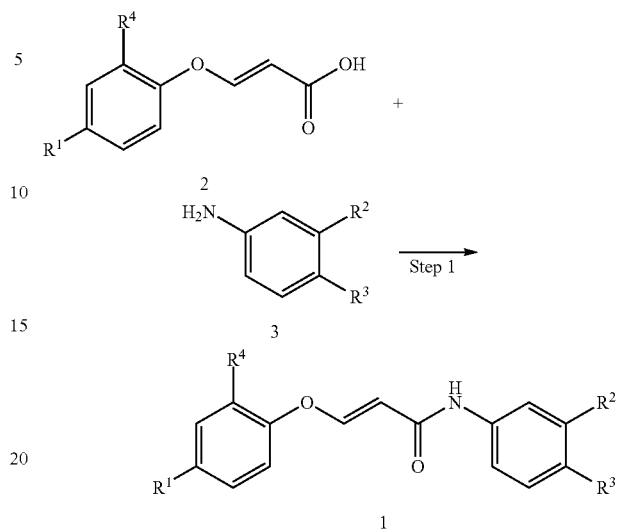

[Reaction Formula 1]

In reaction formula 1, $R^1 \sim R^4$ are as defined in formula 1.

At this time, diisopropylamine (DIPEA) or triethylamine (TEA) is used as the said Hunig base.

The said condensation reagent can be one or more of those preferably selected from the group consisting of O-(7-azabenzotriazol-1-yl)-N,N,N',N'-tetramethyl-uronium-tetrafluoroborate (HATU), 1-[3-(dimethylamino)propyl]-3-ethylcarbodiimide hydrochloride (EDC), O-benzotriazol-N,N,N',N'-tetramethyl-uronium-hexafluoro-phosphate (HBTU), 1-hydroxybenzotriazole (HOBt), benzotriazol-1-yl-oxy-tris-pyrrolidino-phosphoniumhexafluoro phosphate (PyBOP), and 1-hydroxy-7-azabenzo triazole.

Further, the organic solvent used herein is preferably dimethylformamide (DMF) or methylenechloride ($CH_2Cl_2$).

The compound of formula 2 or the compound of formula 3 can be either purchased or synthesized by the conventional method. For example, as shown in reaction formula 2, the compound of formula 2 can be prepared by the following steps: preparing the compound of formula 5 by Michael addition reaction of the compound of formula 4 (step 1): and preparing the compound of formula 2 by reacting the compound of formula 5 with LiOH in the presence of an organic solvent (step 2):

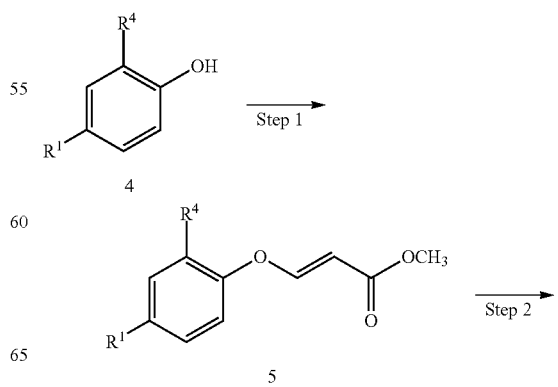

[Reactuion Formula 2]

-continued

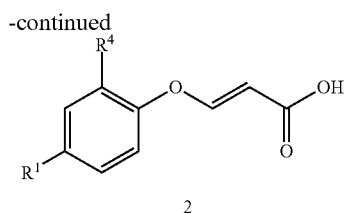

2

In reaction formula 2, $R^1$~$R^4$ are as defined in formula 1.

The method to prepare the novel aryloxyphenoxyacrylic compound of the present invention is not limited to the above, and the well-informed conventional method or non-informed method can be used as long as it can produce the said novel aryloxyphenoxyacrylic compound.

The novel aryloxyphenoxyacrylic compound prepared according to the method of the present invention is isolated and purified by high performance liquid chromatography (HPLC) and then its molecular structure can be confirmed by nuclear magnetic resonance (NMR).

The present invention also provides a pharmaceutical composition for the prevention or treatment of cancer comprising the compound of formula 1 or a pharmaceutically acceptable salt thereof as an active ingredient.

The compound of formula 1 of the present invention or a pharmaceutically acceptable salt thereof demonstrated anticancer activity not by non-selective cytotoxicity but by inhibiting the transcription factor HIF-1 activity playing an important role in cancer growth and metastasis.

The inhibition of HIF-1 activity includes the inhibition of HRE (Hypoxia Responsive Element, 5'-ACGTG-3') transcription activity, the inhibition of HIF-1α protein accumulation, and the inhibition of HIF-1 target gene expression.

In this invention, the inhibition effect of the compound of formula 1 on HIF-1 HRE transcription activity was examined. As a result, the compound of the present invention demonstrated excellent HIF-1 activity inhibition effect, compared with the conventional compounds having the similar structure in hypoxic condition (see FIG. 1). Therefore, the compound of formula 1 of the present invention was confirmed to inhibit HRE transcription activity of HIF-1 in hypoxic condition and to inhibit cancer growth and metastasis by inhibiting the expressions of malignant tumor related genes, so that it can be effectively used as an active ingredient of an anticancer agent.

Figure 2:
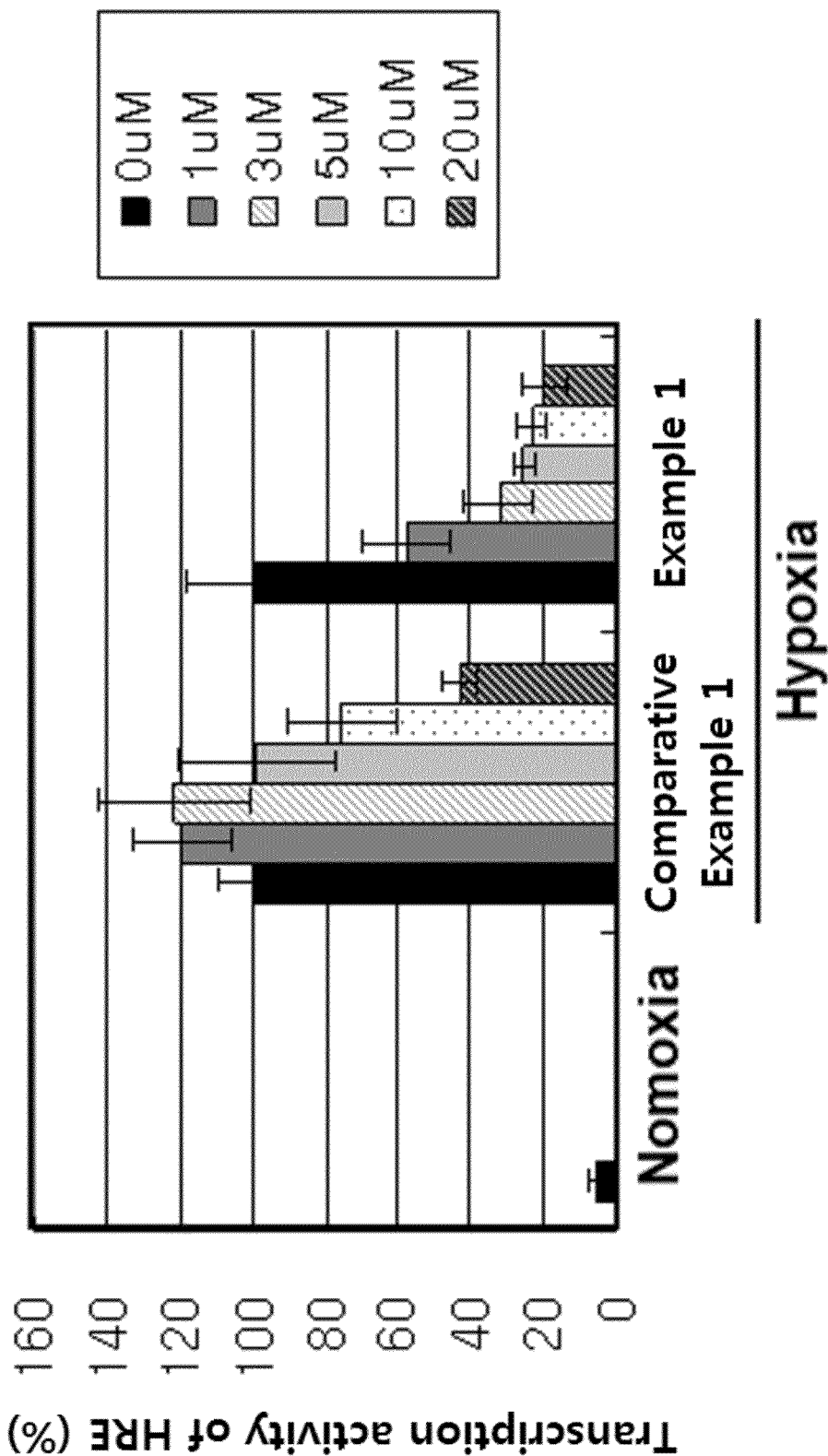
FIG. 2 is a graph illustrating the inhibiting activity of the compound of an example of the present invention on HRE transcription.

The compound of formula 1 of the present invention did not affect the synthesis of β-actin but inhibited the production of HIF-1α dose-dependently in hypoxic condition (see FIG. 2). Therefore, it has been confirmed that anticancer activity of the compound of the present invention is attributed not to the non-selective cytotoxicity but to the selective inhibition of HIF-1α accumulation that leads to the inhibition of cancer growth and metastasis. That is, the compound of the present invention shows anticancer activity with minimizing side effects.

Figure 3:
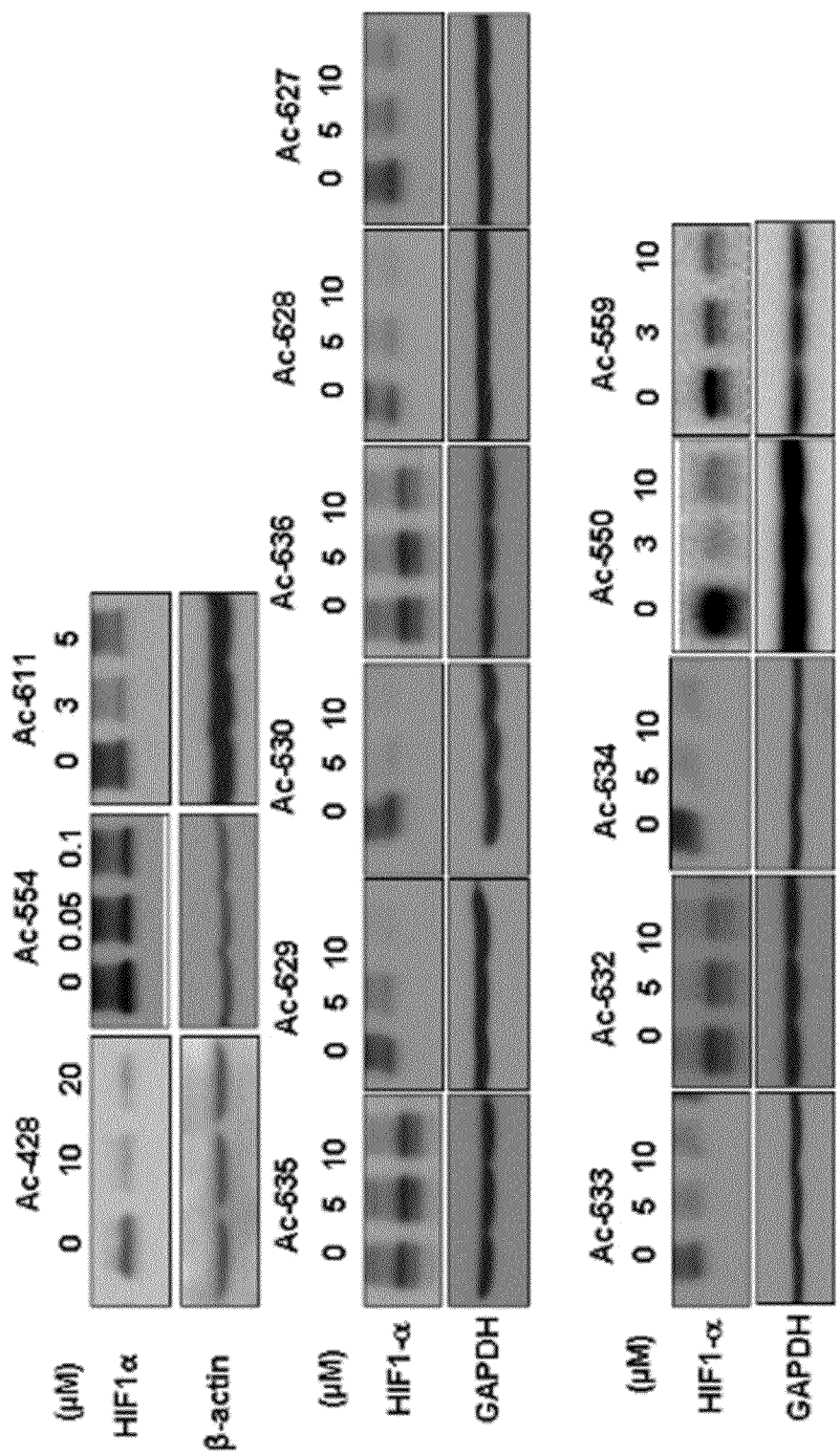
FIG. 3 is a diagram illustrating the inhibition of HIF-1α accumulation by the compounds of an example of the present invention.

Further, the compound of formula 1 of the present invention was also confirmed to inhibit the expression of EPO (erythropoietin) known to accelerate the generation of erythrocyte and VEGF (vascular endothelial growth factor A) that is one of important HIF-1 target genes playing an important role in cancer growth and metastasis (see FIG. 3). Therefore, the compound of the present invention can be effectively used as an active ingredient of an anticancer agent since the compound has the activity of inhibiting the expressions of EPO and VEGF, one of HIF-1 target genes involved in cancer growth and metastasis.

The compound of formula 1 of the present invention or a pharmaceutically acceptable salt thereof can effectively inhibit the activity of HIF-1, and hence it can be used as a therapeutic agent for various cancers including colorectal cancer, liver cancer, stomach cancer, breast cancer, colon cancer, bone cancer, pancreatic cancer, head or neck cancer, uterine cancer, ovarian cancer, rectal cancer, esophageal cancer, small bowel neoplasm, anal cancer, colon cancer, carcinoma of the fallopian tubes, endometrial carcinoma, cervical carcinoma, vaginal carcinoma, vulva carcinoma, Hodgkin's disease, prostate cancer, bladder cancer, kidney cancer, ureter cancer, renal cell carcinoma, kidney pelvic carcinoma, and CNS tumors.

The present invention also provides a pharmaceutical composition having the therapeutic effect on diabetic retinopathy or rheumatoid arthritis by inhibiting HIF-1 activity which comprises the compound of formula 1 or a pharmaceutically acceptable salt thereof as an active ingredient.

The inhibition of HIF-1 activity herein includes a series of inhibition such as the inhibition of HRE transcription activity, the inhibition of HIF-1α accumulation, and the inhibition of the expression of HIF-1 target gene protein.

HIF-1 can be used as a target for the development of a therapeutic agent for the disease which may become worse by the activation of angiogenesis. In particular, such angiogenesis factor as VEGF induced by HIF-1 activated in hypoxic condition is especially involved in the progress of diabetic retinopathy or rheumatoid arthritis. Diabetic retinopathy or arthritis is getting worse by the expression of VEGF induced by HIF-1 in hypoxic condition. So, the compound inhibiting HIF-1 activated in hypoxic condition can be used as a therapeutic agent for diabetic retinopathy or rheumatoid arthritis (Eiji Ikeda, Pathology International, 2005, Vol 55, 603-610).

As explained hereinbefore, the compound of formula 1 of the present invention can selectively inhibit the expression of VEGF (Vascular endothelial growth factor A), the angiogenesis factor, in hypoxic condition without affecting the expression of GAPDH that is the control gene, so that it can be effectively used as an active ingredient of a therapeutic agent for diabetic retinopathy or arthritis which is aggravated by the up-regulation of VEGF caused by HIF-1 in hypoxic condition.

The present invention further provides a method for treating cancer containing the step of administering a therapeutically effective dose of the novel compound represented by formula 1 or the pharmaceutically acceptable salt thereof to a patient having cancer in need of treatment.

At this time, the cancer herein is exemplified by such solid tumors particularly related to the accumulation of HIF-1α protein as colorectal cancer, liver cancer, stomach cancer, breast cancer, colon cancer, bone cancer, pancreatic cancer, head or neck cancer, uterine cancer, ovarian cancer, rectal cancer, esophageal cancer, small bowel neoplasm, anal cancer, colon cancer, carcinoma of the fallopian tubes, endometrial carcinoma, cervical carcinoma, vaginal carcinoma, vulva carcinoma, Hodgkin's disease, prostate cancer, bladder cancer, kidney cancer, ureter cancer, renal cell carcinoma, kidney pelvic carcinoma, and CNS tumors.

The present invention also provides a method for treating diabetic retinopathy containing the step of administering a therapeutically effective dose of the novel compound represented by formula 1 or the pharmaceutically acceptable salt thereof to a patient having diabetic retinopathy in need of treatment.

At this time, the novel compound represented by formula 1 or the pharmaceutically acceptable salt thereof is characterized by the capability of inhibiting angiogenesis by suppressing HIF-1 activity and VEGF expression.

In addition, the present invention provides a method for treating rheumatoid arthritis containing the step of administering a therapeutically effective dose of the novel compound represented by formula 1 or the pharmaceutically acceptable salt thereof to a patient having rheumatoid arthritis in need of treatment.

At this time, the novel compound represented by formula 1 or the pharmaceutically acceptable salt thereof is characterized by the capability of inhibiting angiogenesis by suppressing HIF-1 activity.

The pharmaceutical composition of the present invention can be prepared in many different formulations for oral or parenteral administration. The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the compound represented by formula 1 as an active ingredient of the present invention can be administered by parenterally and the parenteral administration includes subcutaneous injection, intravenous injection, intramuscular injection or intrathoracic injection. To prepare the composition as a formulation for parenteral administration, the compound represented by formula 1 or the pharmaceutically acceptable salt thereof is mixed with a stabilizer or a buffering agent to produce a solution or suspension, which is then formulated as ampoules or vials. The composition of the present invention can be sterilized and/or include an additive such as an antiseptic, a stabilizing agent, a wetting agent or an emulsifying agent, a salt for the regulation of osmotic pressure, and/or a buffer, and other therapeutically useful materials. The composition can be formulated by the conventional procedure including mixing, granulizing, or coating. The effective dose of the compound of formula 1 for an mammal including human is preferably 0.1~500 mg/kg/day, and more preferably 0.5~100 mg/kg/day. The daily dose can be administered once a day or a few times a day via oral or parenteral administration.

The pharmaceutical composition of the present invention can be administered alone or treated together with surgical operation, radio-therapy, hormone therapy, chemo-therapy and biological regulators.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Preparation Example 1

Preparation of (E)-3-(4-adamantan-1-yl-phenoxy)-acrylic acid methylester

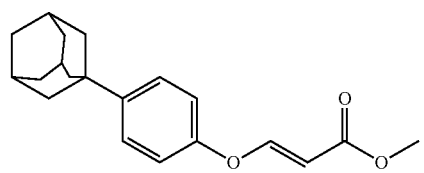 [SMILES: COC(=O)/C=C/Oc1ccc(C23CC4CC(CC(C4)C2)C3)cc1]

4-(Adamantan-1-yl)-phenol (1.0 mg, 4.38 mmol) and methyl propiolate (737 mg, 0.74 ml, 8.76 mmol) were dissolved in 25 ml of toluene, to which $Ph_3P$ (1.15 g, 4.38 mmol) was added, followed by reflux at 115° C. for 3 hours. The reaction solution was concentrated and extracted with EtoAC and NaCl solution. The organic layer was dried over anhydrous $MgSO_4$, and concentrated. The residue was purified by silica gel column chromatography (n-Hexane:EtOAc=50:1) to give the target compound as a white solid (1.24 g, yield: 90.6%).

$^1$H-NMR (CDCl$_3$, 300 MHz) δ 7.81 (1H, d, J=12.3 Hz, CH), 7.35 (2H, d, J=9.3 Hz, aromatic-H), 7.01 (2H, d, J=8.7 Hz, aromatic-H), 5.53 (1H, d, J=12.3 Hz, CH), 3.73 (3H, s, OCH$_3$), 2.10 (3H, m, adamantly-H), 1.89 (6H, m, adamantly-H), 1.77 (6H, m, adamantly-H).

Preparation Example 2

Preparation of (E)-3-(4-t-butylphenoxy)acrylic acid methylester

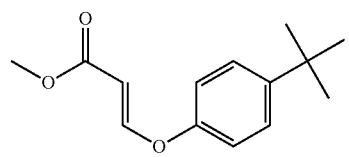 [SMILES: COC(=O)/C=C/Oc1ccc(C(C)(C)C)cc1]

The target compound was obtained from t-butylphenol by the same manner as described in Preparation Example 1 as a yellow oil (750.7 mg, yield: 69.1%).

¹H-NMR (CDCl₃, 300 MHz) δ 7.80 (1H, d, J=12.0 Hz, CH), 7.38 (2H, d, J=9.0 Hz, aromatic-H), 6.99 (2H, d, J=8.7 Hz, aromatic-H), 5.53 (1H, d, J=12.0 Hz, CH), 3.73 (3H, s, OCH₃), 1.32 (9H, s, CH₃).

Preparation Example 3

Preparation of (E)-3-(4-(2,4,4-Trimethylpentan-2-yl)phenoxy)acrylic acid methylester

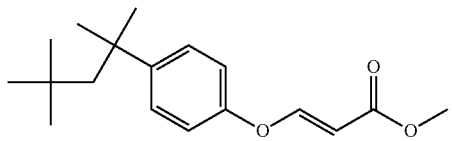 [SMILES: COC(=O)/C=C/Oc1ccc(C(C)(C)CC(C)(C)C)cc1]

The target compound was obtained from 4-(2,4,4-trimethylpentan-2-yl)phenol by the same manner as described in Preparation Example 1 as a yellow oil (365.5 mg, yield: 51.9%).

¹H-NMR (CDCl₃, 300 MHz) δ 7.8 (1H, d, J=12.3 Hz, CH), 7.36 (2H, d, J=8.7 Hz, aromatic-H), 6.97 (2H, d, J=8.4 Hz, aromatic-H), 5.53 (1H, d, J=12.0 Hz, CH), 3.73 (3H, s, OCH₃), 1.73 (2H, s, CH₂), 1.36 (6H, s, CH₃), 0.71 (9H, s, CH₃).

Preparation Example 4

Preparation of (E)-3-(4-Adamantan-1-yl-2-methylphenoxy)acrylic acid methylester

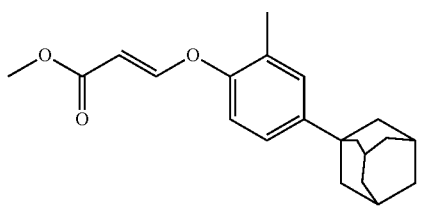 [SMILES: COC(=O)/C=C/Oc1ccc(C23CC4CC(CC(C4)C2)C3)cc1C]

The target compound was obtained from 4-adamantan-1-yl-2-methyl phenol by the same manner as described in Preparation Example 1 as a yellow oil (442.8 mg, yield: 100%).

¹H-NMR (CDCl₃, 300 MHz) δ 7.77 (1H, d, J=12.3 Hz, CH), 7.16 7.19 (2H, m, aromatic-H), 6.92 (1H, d, J=9.0 Hz, aromatic-H), 5.36 (1H, d, J=12.0 Hz, CH), 3.71 (3H, s, OCH₃), 2.23 (3H, s, CH₃), 2.10 (3H, m, adamantly-H), 1.89 (6H, m, adamantly-H), 1.77 (6H, m, adamantly-H)

Preparation Example 5

Preparation of (E)-3-(4-Adamantan-1-yl-phenoxy)-acrylic acid

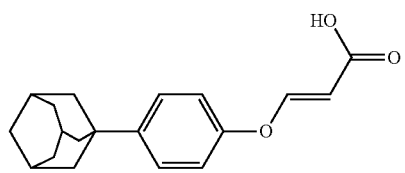 [SMILES: O=C(O)/C=C/Oc1ccc(C23CC4CC(CC(C4)C2)C3)cc1]

3-(4-Adamantan-1-yl-phenoxy)-acrylic acid methylester (569 mg, 1.82 mmol) was dissolved in THF/H₂O mixed solution (3:1, 20 ml), to which lithium hydroxide monohydrate (153 mg, 3.65 mmol) dissolved in purified water (5 ml) was added, followed by stirring for 12 hours. The reaction solution was treated with 10% HCl solution and extracted with ethylacetate and NaCl solution. The organic layer was dried over anhydrous MgSO₄, and concentrated. The residue was purified by silica gel column chromatography (n-Hexane:EtOAc=3:1) to give the target compound as a white solid (526 mg, yield: 96.7%).

¹H-NMR (DMSD-d₆, 300 MHz) δ 12.07 (1H, s, COOH), 7.55 (1H, d, J=7.2 Hz, CH), 7.40 (2H, d, J=5.4 Hz, aromatic-H), 7.11 (2H, d, J=5.1 Hz, aromatic-H), 5.44 (1H, d, J=7.2 Hz, CH), 2.06 (3H, m, adamantly-H), 1.85 (6H, m, adamantly-H), 1.73 (6H, m, adamantly-H)

Preparation Example 6

Preparation of (E)-3-(4-tert-Butylphenoxy)acrylic acid

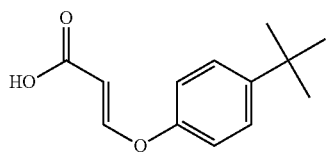 [SMILES: CC(C)(C)c1ccc(O/C=C/C(=O)O)cc1]

The target compound was obtained from (E)-3-(4-t-butylphenoxy)acrylic acid methylester by the same manner as described in Preparation Example 5 as a yellow oil (75.1 mg, yield: 11.0%).

¹H-NMR (CDCl₃, 300 MHz) δ 7.89 (1H, d, J=12.3 Hz, CH), 7.39 (2H, d, J=8.4 Hz, aromatic-H), 7.00 (2H, d, J=8.7 Hz, aromatic-H), 5.50 (1H, d, J=12.3 Hz, CH), 1.32 (9H, s, CH₃)

Preparation Example 7

Preparation of (E)-3-(4-(2,4,4-Trimethylpentan-2-yl)phenoxyl)acrylic acid

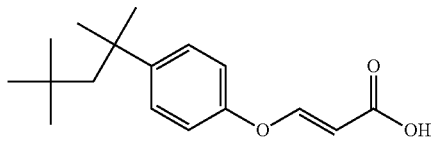 [SMILES: CC(C)(C)CC(C)(C)c1ccc(O/C=C/C(=O)O)cc1]

The target compound was obtained from (E)-3-(4-(2,4,4-trimethylpentan-2-yl)phenoxy)acrylic acid methylester by the same manner as described in Preparation Example 5 as a yellow oil (1.92 mg, yield: 43.3%).

¹H-NMR (CDCl₃, 300 MHz) δ 7.89 (1H, d, J=11.7 Hz, CH), 7.37 (2H, d, J=9.0 Hz, aromatic-H), 6.98 (2H, d, J=8.7 Hz, aromatic-H), 5.50 (1H, d, J=12.3 Hz, CH), 1.73 (2H, s, CH2), 1.36 (6H, s, CH₃), 0.71 (9H, s, CH₃)

Preparation Example 8

Preparation of (E)-3-(4-Adamantan-1-yl-2-methylphenoxy)acrylic acid

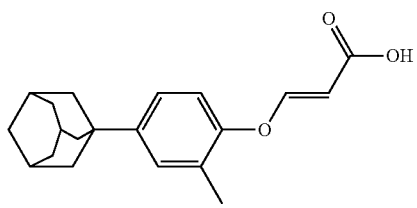 [SMILES: Cc1cc(C23CC4CC(CC(C4)C2)C3)ccc1O/C=C/C(=O)O]

The target compound was obtained from (E)-3-(4-adamantan-1-yl-2-methylphenoxy)acrylic acid methylester by the same manner as described in Preparation Example 5 as a yellow oil (167.4 mg, yield: 50.2%).

¹H-NMR (CDCl₃, 300 MHz) δ 7.85 (1H, d, J=12.0 Hz, CH), 7.18 7.20 (2H, m, aromatic-H), 6.93 (1H, d, J=8.7 Hz, aromatic-H), 5.33 (1H, d, J=12.3 Hz, CH), 2.23 (3H, s, CH₃), 2.10 (3H, m, adamantly-H), 1.89 (6H, m, adamantly-H), 1.77 (6H, m, adamantly-H)

Example 1

Preparation of (E)-3-[3-(4-Adamantan-1-yl-phenoxy)-acryloylamino]-benzoic acid methyl ester (AC-428)

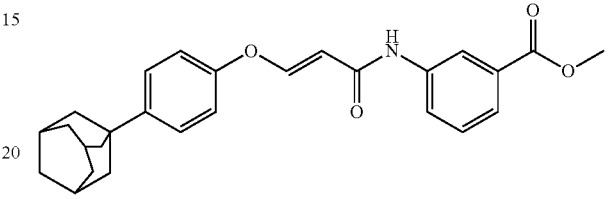

3-(4-Adamantan-1-yl-phenoxy)-acrylic acid (110.6 mg, 0.5 mmol), 3-aminobenzoic acid methyl ester (151.2 mg, 1.0 mmol) and HATU (143.8 mg, 0.75 mmol) were mixed in 5 ml of DMF, to which DIPEA (0.13 ml, 0.75 mmol) was added, followed by stirring for 12 hours at room temperature. The reaction mixture was extracted with ethylacetate and 10% HCl, thereafter the organic layer was washed with NaCl solution and water, dried over anhydrous MgSO₄, and concentrated. The residue was purified by silcagel column chromatography (n-Hexane:EtOAc=10:1) to give the target compound as a white solid (21.5 mg, yield: 10.6%).

¹H-NMR (CDCl₃, 300 MHz) δ 8.06 (1H, s, aromatic-H), 7.89 7.95 (2H, m, aromatic-H, CH), 7.77 (1H, d, J=7.5 Hz, aromatic-H), 7.33 7.42 (3H, m, aromatic-H), 7.02 (2H, d, J=8.7 Hz, aromatic-H), 5.68 (1H, d, J=11.7 Hz, CH), 3.90 (3H, s, CH₃), 2.11 (3H, m, adamantly-H), 1.90 (6H, m, adamantly-H), 1.77 (6H, m, adamantly-H).

Example 2

Preparation of (E)-3-(3-(4-tert-Butylphenoxy)acrylamido)benzoic acid methylester (AC-629)

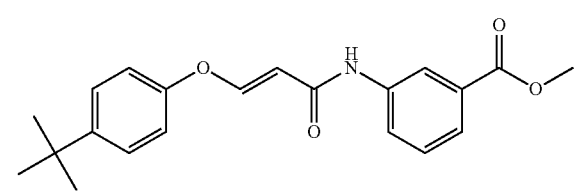 [SMILES: COC(=O)c1cccc(NC(=O)/C=C/Oc2ccc(C(C)(C)C)cc2)c1]

The target compound was obtained from (E)-3-(4-t-butylphenoxy)acrylic acid by the same manner as described in Example 1 as a white solid (41.0 mg, yield: 40.0%).

¹H-NMR (CDCl₃, 300 MHz) δ 8.05 (1H, m, aromatic-H), 7.93 7.89 (2H, m, aromatic-H, CH), 7.77 (1H, d, J=8.1 Hz, aromatic-H), 7.43 7.37 (3H, m, aromatic-H), 7.18 (1H, s, NH), 7.02 (2H, d, J=9.0 Hz, aromatic-H), 7.00 (2H, d, J=8.7 Hz, aromatic-H), 5.66 (1H, d, J=11.4 Hz, CH), 3.91 (3H, s, OCH₃), 1.32 (9H, s, (CH₃)₃)

Example 3

Preparation of (E)-3-(3-(4-(2,4,4-Trimethylpentan-2-yl)phenoxy)acryl amido)benzoic acid methylester (AC-630)

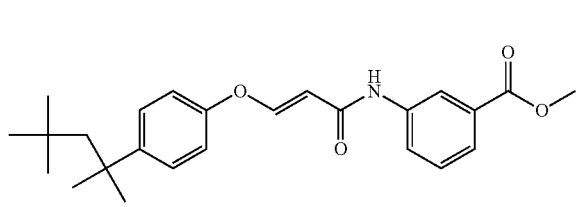 [SMILES: COC(=O)c1cccc(NC(=O)/C=C/Oc2ccc(C(C)(C)CC(C)(C)C)cc2)c1]

The target compound was obtained from (E)-3-(4-(2,4,4-trimethylpentan-2-yl)phenoxy)acrylic acid by the same manner as described in Example 1 as a white solid (733.0 mg, yield: 62.8%).

¹H-NMR (DMSO-d₆, 300 MHz) δ 8.05 (1H, m, aromatic-H), 7.89 7.93 (2H, m, aromatic-H, CH), 7.78 (1H, d, J=7.8 Hz, aromatic-H), 7.41 (1H, d, J=8.4 Hz, aromatic-H), 7.37 (2H, d, J=8.4 Hz, aromatic-H), 7.11 (1H, s, NH), 7.00 (2H, d, J=8.7 Hz, aromatic-H), 5.66 (1H, d, J=11.4 Hz, CH), 3.91 (3H, s, OCH3), 1.73 (2H, s, CH₂), 1.37 (6H, s, (CH₃)₂), 0.72 (9H, s, (CH₃)₃)

Example 4

Preparation of (E)-3-(3-(4-Adamantan-1-yl-2-methylphenoxy)acrylamido)benzoic acid methylester (AC-635)

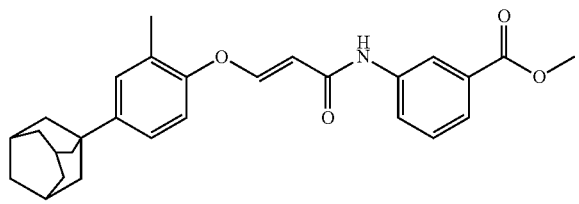 [SMILES: COC(=O)c1cccc(NC(=O)/C=C/Oc2ccc(C34CC5CC(CC(C5)C3)C4)cc2C)c1]

The target compound was obtained from (E)-3-(4-adamantan-1-yl-2-methylphenoxy)acrylic acid by the same manner as described in Example 1 as a white solid (63.7 mg, yield: 74.5%).

¹H-NMR (DMSO-d₆, 300 MHz) δ 10.05 (1H, s, NH), 8.27 (1H, m, aromatic-H), 7.82 7.84 (1H, m, aromatic-H), 7.72 (1H, d, J=12.3 Hz, CH), 7.60-7.62 (1H, m, aromatic-H), 7.43 (1H, t, J=8.1 Hz, aromatic-H), 7.32 (1H, m, aromatic-H), 7.26 (1H, dd, J=3.0 & 8.55 Hz, aromatic-H), 7.06 (1H, d, J=8.1 Hz, aromatic-H), 5.58 (1H, d, J=12.3 Hz, CH), 3.84 (3H, s, OCH₃), 2.20 (3H, s, CH₃), 2.06 (3H, m, adamantly-H), 1.87 (6H, m, adamantly-H), 1.74 (6H, m, adamantly-H)

Example 5

Preparation of (E)-4-(3-(4-Admantan-1-ylphenoxy) acrylamido)benzoic acid methylester (AC-636)

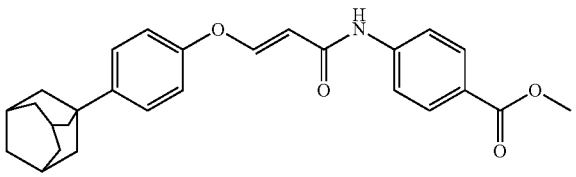 [SMILES: COC(=O)c1ccc(NC(=O)/C=C/Oc2ccc(C34CC5CC(CC(C5)C3)C4)cc2)cc1]

The target compound was obtained from 4-aminobenzoic acid methylester by the same manner as described in Example 1 as a white solid (9.7 mg, yield: 11.2%).

¹H-NMR (DMSO-d₆, 300 MHz) δ 10.23 (1H, s, NH), 7.91 (2H, d, J=8.7 Hz, aromatic-H), 7.73 7.79 (3H, m, aromatic-H, CH), 7.42 (2H, d, J=8.7 Hz, aromatic-H), 7.14 (2H, d, J=8.4 Hz, aromatic-H), 5.83 (1H, d, J=11.7 Hz, CH), 3.82 (3H, s, CH₃), 2.06 (3H, m, adamantly-H), 1.86 (6H, m, adamantly-H), 1.74 (6H, m, adamantly-H)

Example 6

Preparation of (E)-3-(4-Adamantan-1-ylphenoxy)-N-(3-sulfamoylphenyl)acrylamide (AC-627)

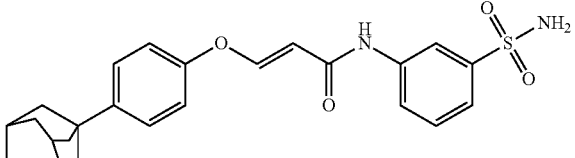

The target compound was obtained from 3-aminobenzenesulfonamide by the same manner as described in Example 1 as a white solid (18.2 mg, yield: 20.1%).

¹H-NMR (DMSD-d₆, 300 MHz) δ 10.19 (1H, s, NH), 8.17 (1H, s, aromatic-H), 7.75 7.79 (2H, m, aromatic-H, CH), 7.48 7.49 (2H, m, aromatic-H), 7.43 (2H, d, J=8.7 Hz, aromatic- H), 7.14 (2H, d, J=9 Hz, aromatic-H), 5.81 (1H, d, J=11.4 Hz, CH), 2.06 (3H, m, adamantly-H), 1.86 (6H, m, adamantly-H), 1.74 (6H, m, adamantly-H)

Example 7

Preparation of (E)-3-(4-Adamantan-1-ylphenoxy)-N-(3-(methylsulfonyl)phenyl)acrylamide (AC-628)

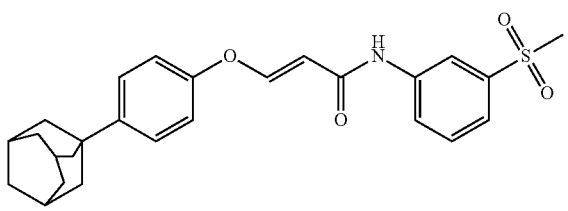 [SMILES: CS(=O)(=O)c1cccc(NC(=O)/C=C/Oc2ccc(C34CC5CC(CC(C5)C3)C4)cc2)c1]

The target compound was obtained from 3-(methylsulfonyl)benzeneamine by the same manner as described in Example 1 as a white solid (18.2 mg, yield: 20.2%).

$^1$H-NMR (DMSD-$d_6$, 300 MHz) δ 10.29 (1H, s, NH), 8.26 (1H, s, aromatic-H), 7.86 7.90 (1H, m, aromatic-H), 7.79 (1H, d, J=12.0 Hz, CH), 7.57 7.59 (2H, m, aromatic-H), 7.43 (2H, d, J=8.7 Hz, aromatic-H), 7.14 (2H, d, J=9 Hz, aromatic-H), 5.82 (1H, d, J=12.3 Hz, CH), 2.19 (3H, s, CH$_3$), 2.06 (3H, m, adamantly-H), 1.86 (6H, m, adamantly-H), 1.74 (6H, m, adamantly-H)

Example 8

Preparation of (E)-5-[3-(4-Adamantan-1-yl-phenoxy)-acryloylamino]-2-hydroxy-benzoic acid methylester (AC-551)

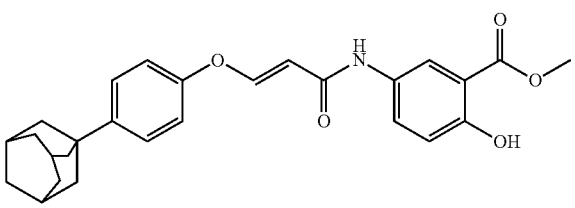 [SMILES: COC(=O)c1cc(NC(=O)/C=C/Oc2ccc(C34CC5CC(CC(C5)C3)C4)cc2)ccc1O]

The target compound was obtained from 5-amino-2-hydroxy-benzoic acid methylester by the same manner as described in Example 1 as a white solid (52.6 mg, yield: 34.6%).

$^1$H-NMR (CDCl$_3$, 300 MHz) δ 10.61 (1H, s, NH), 8.11 (1H, s, OH), 7.89 (1H, d, J=11.7 Hz, CH), 7.50 7.52 (1H, m, aromatic-H), 7.36 (2H, d, J=8.7 Hz, aromatic-H), 7.03 (2H, d, J=8.7 Hz, aromatic-H), 6.95 (1H, d, J=8.7 Hz, aromatic-H), 6.93 (1H, s, aromatic-H), 5.62 (1H, d, J=11.1 Hz, CH), 3.94 (3H, s, CH$_3$), 2.11 (3H, m, adamantly-H), 1.90 (6H, m, adamantly-H), 1.77 (6H, m, adamantly-H)

Example 9

Preparation of (E)-3-[3-(4-Adamantan-1-yl-phenoxy)-acryloylamino]-benzoic acid (AC-553)

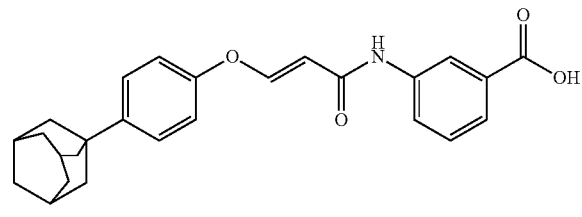 [SMILES: O=C(/C=C/Oc1ccc(C23CC4CC(CC(C4)C2)C3)cc1)Nc1cccc(C(=O)O)c1]

The target compound was obtained from (E)-3-[3-(4-adamantan-1-yl-phenoxy)-acryloylamino]-benzoic acid methylester by the same manner as described in Example 1 as a white solid (19.2 mg, yield: 65.7%).

$^1$H-NMR (DMSO-$d_6$, 300 MHz) δ 10.08 (1H, s, NH), 8.23 (1H, s, aromatic-H), 7.86 (1H, d, J=8.7 Hz, aromatic-H), 7.75 (1H, d, J=12.0 Hz, CH), 7.60 (1H, d, J=7.5 Hz, aromatic-H), 7.39 7.44 (3H, m, aromatic-H), 7.14 (2H, d, J=9.0 Hz, aromatic-H), 5.81 (1H, d, J=11.7 Hz, CH), 2.06 (3H, m, adamantly-H), 1.86 (6H, m, adamantly-H), 1.74 (6H, m, adamantly-H)

Example 10

Preparation of (E)-3-(3-(4-adamantan-1-ylphenoxy)acrylamido)benzoic acid ethylester (AC-610)

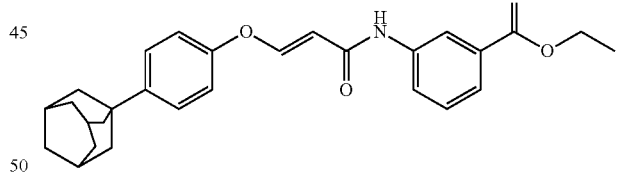

The target compound was obtained from 3-aminobenzoic acid ethylester by the same manner as described in Example 1 as a white solid (44.6 mg, yield: 50.0%).

$^1$H-NMR (DMSO-$d_6$, 300 MHz) δ 10.12 (1H, s, NH), 8.26 (1H, d, J=1.2 Hz, aromatic-H), 7.89 (1H, d, J=8.4 Hz, aromatic-H), 7.77 (1H, dd, J=1.5 & 12.2 Hz, CH), 7.62 (1H, d, J=7.5 Hz, aromatic-H), 7.41 7.47 (3H, m, aromatic-H), 7.14 (2H, d, J=7.2 Hz, aromatic-H), 5.81 (1H, d, J=12.0 Hz, CH), 4.31 (2H, q, J=6.9 Hz, CH$_2$), 3.90 (3H, s, CH3), 2.06 (3H, m, adamantly-H), 1.86 (6H, m, adamantly-H), 1.74 (6H, m, adamantly-H), 1.32 (3H, t, J=7.2 Hz, CH$_3$)

Example 11

Preparation of (E)-3-(3-(4-adamantan-1-ylphenoxy)acrylamido)benzoic acid 2-methoxyethylester (AC-611)

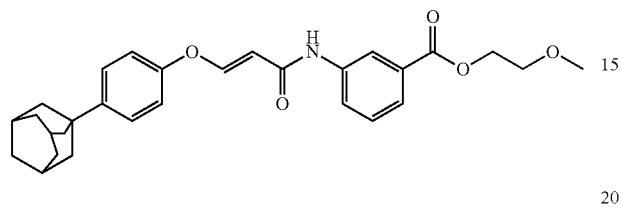

The target compound was obtained from 3-aminobenzoic acid 2-methoxyethylester by the same manner as described in Example 1 as a white solid (569.8 mg, yield: 51.1%).

$^1$H-NMR (DMSO-d$_6$, 300 MHz) δ 10.14 (1H, s, NH), 8.24 (1H, s, aromatic-H), 7.92 (1H, d, J=8.7 Hz, aromatic-H), 7.77 (1H, d, J=11.4 Hz, CH), 7.63 (1H, d, J=7.8 Hz, aromatic-H), 7.41 7.48 (3H, m, aromatic-H), 7.14 (2H, d, J=9.0 Hz, aromatic-H), 5.81 (1H, d, J=12.0 Hz, CH), 4.39 (2H, m, CH$_2$), 4.39 (2H, m, CH$_2$), 3.31 (3H, s, CH$_3$), 2.06 (3H, m, adamantly-H), 1.86 (6H, m, adamantly-H), 1.74 (6H, m, adamantly-H)

Example 12

Preparation of (E)-3-(3-(4-adamantan-1-yl-phenoxy)acrylamido)benzoic acid 2-(dimethylamino)ethylester (AC-632)

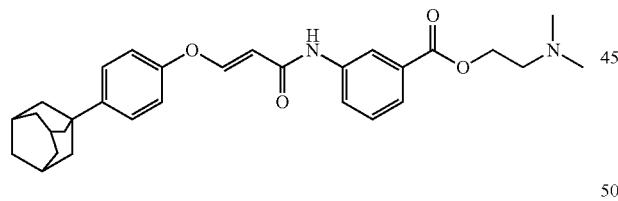

(E)-3-(3-(4-Adamantan-1-yl-phenoxy)acrylamido)benzoic acid (60 mg, 0.144 mmol) and 2-(dimethylamino)ethylchloride.HCl (31.1 mg, 0.216 mmol) were dissolved in DMF (3 ml), to which K$_2$CO$_3$ (39.8 mg, 0.288 mmol) was added, followed by stirring at 60° C. for 12 hours. The reaction mixture was extracted with ethylacetate and NaHCO$_3$ solution, thereafter the organic layer was washed with NaCl solution and water, dried over anhydrous MgSO$_4$, and concentrated. The residue was purified by Prep-TLC (n-Hexane:EtOAc=10:1) to give the target compound as a white solid (21.5 mg, yield: 10.6%).

$^1$H-NMR (DMSO-d$_6$, 300 MHz) δ 10.13 (1H, s, NH), 8.25 (1H, m, aromatic-H), 7.88 7.91 (1H, m, aromatic-H), 7.77 (1H, d, J=12.0 Hz, CH), 7.61-7.63 (1H, m, aromatic-H), 7.41-7.48 (3H, m, aromatic-H), 7.14 (2H, d, J=9.0 Hz, aromatic-H), 5.81 (1H, d, J=12.0 Hz, CH), 4.35 (2H, t, J=6.0 Hz, CH2), 2.61 (2H, t, J=6.0 Hz, CH$_2$), 2.21 (6H, s, N(CH$_3$)$_2$), 2.06 (3H, m, adamantly-H), 1.87 (6H, m, adamantly-H), 1.74 (6H, m, adamantly-H)

Example 13

Preparation of (E)-3-(3-(4-adamantan-1-ylphenoxy)acrylamido)benzoic acid 2-(pyrrolidin-1-yl)ethylester (AC-633)

The target compound was obtained from 2-(pyrrolidine-1-yl)ethylchloride.HCl by the same manner as described in Example 12 as a white solid (9.3 mg, yield: 18.6%).

$^1$H-NMR (DMSO-d$_6$, 300 MHz) δ 10.13 (1H, s, NH), 8.26 (1H, s, aromatic-H), 7.90 (1H, d, J=8.7 Hz, aromatic-H), 7.77 (1H, d, J=12.0 Hz, CH), 7.62 (1H, d, J=7.5 Hz, aromatic-H), 7.45 (1H, t, J=8.1 Hz, aromatic-H), 7.42 (2H, d, J=8.7 Hz, aromatic-H), 7.14 (2H, d, J=9.0 Hz, aromatic-H), 5.81 (1H, d, J=11.4 Hz, CH), 4.37 (2H, t, J=5.7 Hz, CH$_2$), 2.78 (2H, t, J=5.4 Hz, CH$_2$), 2.50 2.53 (4H, m, CH$_2$), 2.06 (3H, m, adamantly-H), 1.86 (6H, m, adamantly-H), 1.74 (6H, m, adamantly-H), 1.68 (4H, m, CH$_2$)

Example 14

Preparation of (E)-3-(3-(4-adamantan-1-ylphenoxy)acrylamido)benzoic acid morpholinoethylester (AC-634)

The target compound was obtained from morpholinoethylchloride.HCl by the same manner as described in Example 12 as a white solid (9.3 mg, yield: 18.6%).

$^1$H-NMR (DMSO-d$_6$, 300 MHz) δ 10.13 (1H, s, NH), 8.27 (1H, m, aromatic-H), 7.86 7.89 (1H, m, aromatic-H), 7.76 (1H, d, J=11.7 Hz, CH), 7.62 (1H, d, J=7.8 Hz, aromatic-H), 7.41-7.48 (3H, m, aromatic-H), 7.14 (2H, d, J=9.0 Hz, aromatic-H), 5.81 (1H, d, J=12.0 Hz, CH), 4.38 (2H, t, J=6.0 Hz, CH$_2$), 3.56 (4H, t, J=5.1 Hz, CH$_2$), 2.68 (2H, t, J=6.0 Hz, CH$_2$), 2.47 (4H, t, J=4.8 Hz, CH$_2$), 2.06 (3H, m, adamantly-H), 1.86 (6H, m, adamantly-H), 1.74 (6H, m, adamantly-H)

Example 15

Preparation of (E)-3-[3-(4-adamantan-1-yl-phenoxy)-acryloylamino]-benzamide (AC-552)

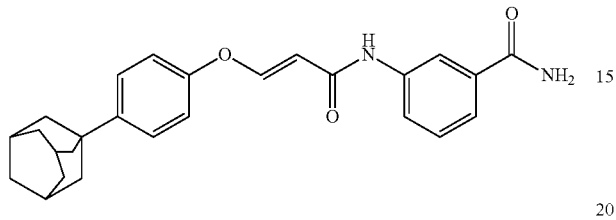

The target compound was obtained from E)-3-[3-(4-adamantan-1-yl-phenoxy)-acryloylamino]-benzoic acid and NH$_4$Cl by the same manner as described in Example 1 as a white solid (9.3 mg, yield: 18.6%).

$^1$H-NMR (DMSO-d$_6$, 300 MHz) δ 10.03 (1H, s, NH), 8.02 (1H, m, aromatic-H), 7.91 (1H, br-s, NH$_2$), 7.79 7.82 (1H, m, aromatic-H), 7.74 (1H, d, J=12.0 Hz, CH), 7.51 (1H, d, J=7.5 Hz, aromatic-H), 7.42 (2H, d, J=9.0 Hz, aromatic-H), 7.36 (1H, d, J=15.6 Hz, aromatic-H), 7.31 (1H, br-s, NH$_2$), 7.13 (2H, d, J=8.4 Hz, aromatic-H), 5.83 (1H, d, J=12.0 Hz, CH), 2.06 (3H, m, adamantly-H), 1.86 (6H, m, adamantly-H), 1.73 (6H, m, adamantly-H)

Example 16

Preparation of (E)-3-[3-(4-adamantan-1-yl-phenoxy)-acryloylamino]-N-isopropyl-benzamide (AC-550)

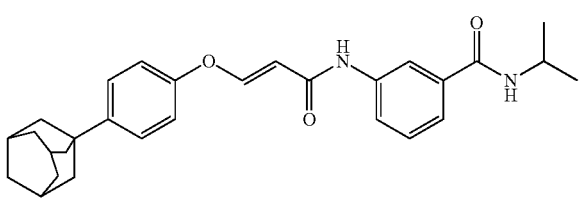 [SMILES: CCOC(=O)c1cccc(NC(=O)/C=C/Oc2ccc(C34CC5CC(CC(C5)C3)C4)cc2)c1]

The target compound was obtained from 3-amino-N-isopropyl-benzamide by the same manner as described in Example 1 as a white solid (57.8 mg, yield: 37.1%).

$^1$H-NMR (DMSO-d$_6$, 300 MHz) δ 10.03 (1H, s, NH), 8.18 (1H, d, J=7.2 Hz, NHCH), 7.96 (1H, s, aromatic-H), 7.82 (1H, d, J=9.0 Hz, aromatic-H), 7.82 (1H, d, J=11.7 Hz, CH), 7.33 7.49 (4H, m, aromatic-H), 7.13 (2H, d, J=9.0 Hz, aromatic-H), 5.83 (1H, d, J=12.3 Hz, CH), 4.01 4.11 (1H, m, CH(CH$_3$)

$_2$), 2.06 (3H, m, adamantly-H), 1.86 (6H, m, adamantly-H), 1.74 (6H, m, adamantly-H), 1.15 (6H, d, J=6.6 Hz, CH$_3$)

Example 17

Preparation of (E)-3-[3-(4-Adamantan-1-yl-phenoxy)-acryloylamino]-N-furan-2-ylmethyl-benzamide (AC-559)

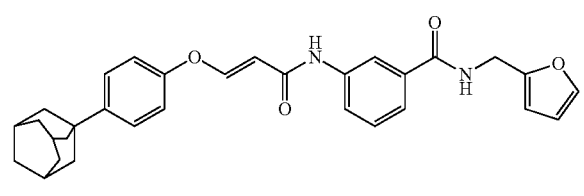 [SMILES: O=C(/C=C/Oc1ccc(C23CC4CC(CC(C4)C2)C3)cc1)Nc1cccc(C(=O)NCc2ccco2)c1]

The target compound was obtained from (E)-3-[3-(4-adamantan-1-yl-phenoxy)-acryloylamino]-benzoic acid and furfurylamine by the same manner as described in Example 1 as a white solid (37.7 mg, yield: 63.3%).

$^1$H-NMR (DMSO-d$_6$, 300 MHz) δ 10.05 (1H, s, NH), 8.92 (1H, t, J=6 Hz, NHCH$_2$), 8.03 (1H, m, aromatic-H), 7.79 7.82 (1H, m, aromatic-H), 7.74 (1H, d, J=12.0 Hz, CH), 7.56 (1H, m, aromatic-H), 7.51 (1H, d, J=8.1 Hz, aromatic-H), 7.42 (2H, d, J=9.0 Hz, aromatic-H), 7.37 (1H, t, J=8.1 Hz, aromatic-H), 7.13 (2H, d, J=8.7 Hz, aromatic-H), 6.39 (1H, m, aromatic-H), 6.26 (1H, d, J=3.3 Hz, aromatic-H), 5.83 (1H, d, J=12.0 Hz, CH), 4.44 (2H, d, J=5.4 Hz, CH$_2$), 2.06 (3H, m, adamantly-H), 1.86 (6H, m, adamantly-H), 1.73 (6H, m, adamantly-H)

Example 18

(E)-3-[3-(4-adamantan-1-yl-phenoxy)-acryloylamino]-N-(2-morpholin-4-yl-ethyl)-benzamide (AC-571)

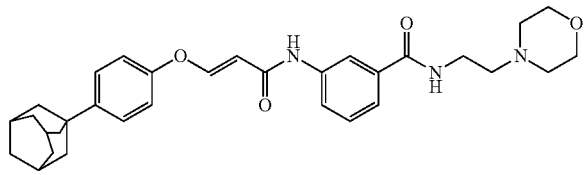 [SMILES: O=C(/C=C/Oc1ccc(C23CC4CC(CC(C4)C2)C3)cc1)Nc1cccc(C(=O)NCCN2CCOCC2)c1]

The target compound was obtained from 3-amino-N-(2-morpholinoethyl)benzamide by the same manner as described in Example 1 as a white solid (42.9 mg, yield: 40.5%).

$^1$H-NMR (CDCl$_3$, 300 MHz) δ 7.98 (1H, s, aromatic-H), 7.90 (1H, d, J=11.7 Hz, CH), 7.79 (1H, d, J=7.2 Hz, aromatic-H), 7.48 (1H, d, J=8.1 Hz, aromatic-H), 7.35 7.42 (3H, m, aromatic-H), 7.04 (2H, d, J=8.7 Hz, aromatic-H), 6.93 (1H, m, NHCH$_2$), 5.70 (1H, d, J=11.7 Hz, CH), 3.75 (4H, t, J=4.5 Hz, CH2), 3.53 3.59 (2H, m, CH$_2$), 2.61 (2H, t, J=6.0 Hz, CH$_2$), 2.52 (4H, t, J=4.5 Hz, CH$_2$), 2.11 (3H, m, adamantly-H), 1.90 (6H, m, adamantly-H), 1.77 (6H, m, adamantly-H)

Example 19

Preparation of (E)-3-[3-(4-adamantan-1-yl-phenoxy)-acryloylamino]-N-(2-pyridin-4-yl-ethyl)-benzamide (AC-554)

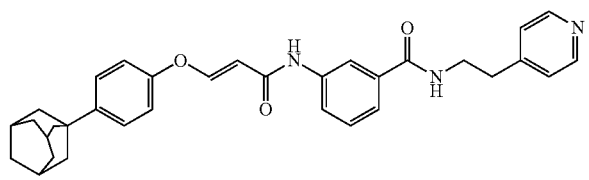 [SMILES: O=C(/C=C/Oc1ccc(C23CC4CC(CC(C4)C2)C3)cc1)Nc1cccc(C(=O)NCCc2ccncc2)c1]

The target compound was obtained from 3-amino-N-(2-pyridine-4-yl-ethyl)-benzamide by the same manner as described in Example 1 as a white solid (81.2 mg, yield: 66.5%).

$^1$H-NMR (DMSO-d$_6$, 300 MHz) δ 10.04 (1H, s, NH), 8.53 (1H, t, J=5.4 Hz, NHCH$_2$), 8.46 (2H, d, J=6.0 Hz, aromatic-H), 8.00 (1H, s, aromatic-H), 7.78 (1H, d, J=9.0 Hz, aromatic-H), 7.75 (1H, d, J=12.0 Hz, CH), 7.41 7.44 (3H, m, aromatic-H), 7.36 (1H, t, J=7.5 Hz, aromatic-H), 7.27 (2H, d, J=5.7 Hz, aromatic-H), 5.83 (1H, d, J=12.0 Hz, CH), 3.49 3.55 (2H, m, CH$_2$), 2.87 (2H, t, J=6.9 Hz, CH2), 2.06 (3H, m, adamantly-H), 1.86 (6H, m, adamantly-H), 1.74 (6H, m, adamantly-H)

Example 20

Preparation of (E)-3-[3-(4-adamantan-1-yl-phenoxy)-acryloylamino]-N-(3-imidazol-1-yl-propyl)-benzamide (AC-555)

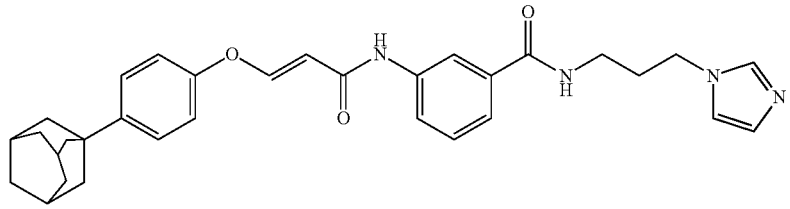 [SMILES: O=C(/C=C/Oc1ccc(C23CC4CC(CC(C4)C2)C3)cc1)Nc1cccc(C(=O)NCCCn2ccnc2)c1]

The target compound was obtained from 3-amino-N-(3-imidazole-1-yl-propyl)-benzamide by the same manner as described in Example 1 as a white solid (41.3 mg, yield: 23.2%).

$^1$H-NMR (DMSO-d$_6$, 300 MHz) δ 10.05 (1H, s, NH), 8.49 (1H, t, J=5.4 Hz, NHCH$_2$), 8.02 (1H, s, aromatic-H), 7.81 (1H, d, J=8.4 Hz, aromatic-H), 7.75 (1H, d, J=12.0 Hz, CH), 7.65 (1H, s, aromatic-H), 7.49 (1H, d, J=7.5 Hz, aromatic-H), 7.42 (2H, d, J=8.7 Hz, aromatic-H), 7.38 (1H, t, J=7.8 Hz, aromatic-H), 7.21 (1H, s, aromatic-H), 7.13 (2H, d, J=8.7 Hz, aromatic-H), 6.89 (1H, s, aromatic-H), 5.83 (1H, d, J=12.0 Hz, CH), 4.01 (2H, t, J=6.9 Hz, CH$_2$), 3.19 3.25 (2H, m, CH$_2$), 2.06 (3H, m, adamantly-H), 1.95 (2H, m, CH$_2$), 1.86 (6H, m, adamantly-H), 1.74 (6H, m, adamantly-H)

Example 21

Preparation of (E)-3-(3-(4-(2,4,4-trimethylpentan-2-yl)phenoxy)acrylamido)benzoic acid

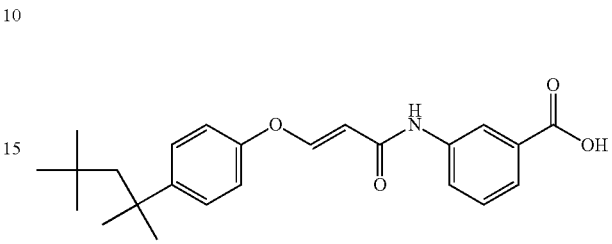

The target compound was obtained from (E)-3-(4-(2,4,4-trimethylpentan-2-yl)phenoxy)acrylic acid methylester by the same manner as described in Example 5 as a white solid (646.7 mg, yield: 86.5%).

$^1$H-NMR (DMSO-d$_6$, 300 MHz) δ 12.92 (1H, s, COOH), 10.09 (1H, s, NH), 8.24 (1H, s, aromatic-H), 7.87 (1H, d, J=8.7 Hz, aromatic-H), 7.74 (1H, d, J=12.0 Hz, CH), 7.61 (1H, d, J=7.8 Hz, aromatic-H), 7.40 7.46 (3H, m, aromatic- H), 7.11 (2H, d, J=8.7 Hz, aromatic-H), 5.85 (1H, d, J=12.3 Hz, CH), 1.73 (2H, s, CH$_2$), 1.33 (6H, s, CH$_3$), 0.69 (9H, s, CH$_3$)

Example 22

Preparation of (E)-2-methoxyethyl 3-(3-(4-(2,4,4-trimethylpentan-2-yl)phenoxy)acrylamido)benzoate (AC-695)

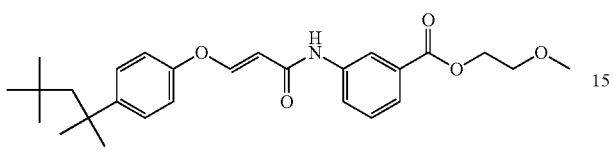

The target compound was obtained from (E)-3-(4-(2,4,4-trimethylpentan-2-yl)phenoxy)acrylic acid and 3-aminobenzoic acid 2-methoxyethylester by the same manner as described in Example 12 as a white solid (61.1 mg, yield: 53.2%).

$^1$H-NMR (CDCl$_3$, 500 MHz) δ 8.02 (1H, d, J=7.6 Hz, aromatic-H), 7.96 (1H, s, aromatic-H), 7.91 (1H, d, J=11.6 Hz, CH), 7.80 (1H, d, J=7.8 Hz, aromatic-H), 7.41 (1H, t, J=7.98 Hz, aromatic-H), 7.37 (2H, d, J=8.7 Hz, aromatic-H), 7.09 (1H, s, NH), 7.00 (2H, d, J=8.7 Hz, aromatic-H), 5.65 (1H, d, J=11.6 Hz, CH), 4.47 (2H, t, J=4.7 Hz, CH$_2$), 3.73 (2H, t, J=4.8 Hz, CH$_2$), 3.44 (3H, s, OCH$_3$), 1.74 (2H, s, CH$_2$), 1.37 (6H, s, CH$_3$), 0.72 (9H, s, CH$_3$)

Example 23

Preparation of (E)-2-morpholinoethyl 3-(3-(4-(2,4,4-trimethylpentan-2-yl)phenoxy)acrylamido)benzoate (AC-694)

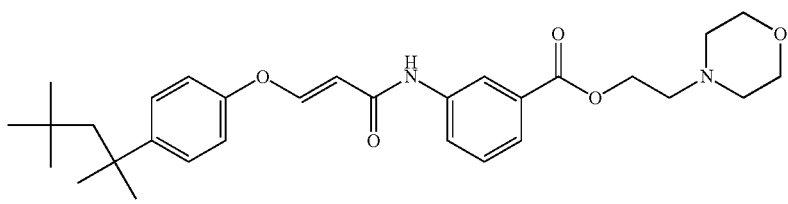 [SMILES: CC(C)(C)CC(C)(C)c1ccc(O/C=C/C(=O)Nc2cccc(C(=O)OCCN3CCOCC3)c2)cc1]

The target compound was obtained from (E)-3-(3-(4-(2,4,4-trimethylpentan-2-yl)phenoxy)acrylamido)benzoic acid and morpholinoethyl chloride.HCl by the same manner as described in Example 1 as a white solid (402.9 mg, yield: 71.4%).

$^1$H-NMR (DMSO-d$_6$, 500 MHz) δ 10.14 (1H, s, NH), 8.27 (1H, s, aromatic-H), 7.88-7.80 (1H, m, aromatic-H), 7.75 (1H, d, J=12.0 Hz, CH), 7.62 (1H, d, J=7.8 Hz, aromatic-H), 7.44-7.47 (3H, m, aromatic-H), 7.11 (2H, d, J=8.8 Hz, aromatic-H), 5.85 (1H, d, J=12.0 Hz, CH), 4.39 (2H, t, J=5.71 Hz, CH$_2$), 3.56 (4H, t, J=4.44 Hz, CH$_2$), 2.68 (2H, t, J=5.75 Hz, CH$_2$), 2.48 (4H, m, CH$_2$), 1.73 (2H, s, CH$_2$), 1.34 (6H, s, CH$_3$), 0.69 (9H, s, CH$_3$)

Comparative Example 1

Preparation of 3-[2-(4-adamantan-1-yl-phenoxy)-acetylamino]-4-hydroxy-benzoic acid methyl ester

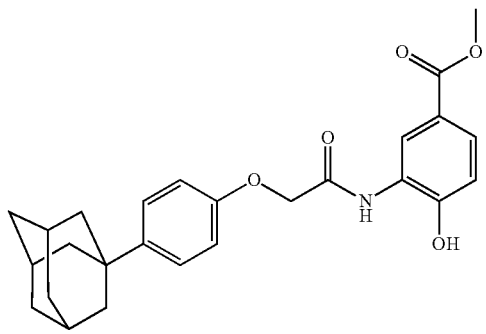 [SMILES: COC(=O)c1ccc(O)c(NC(=O)COc2ccc(C34CC5CC(CC(C5)C3)C4)cc2)c1]

4-Adamantan-1-yl-phenoxy acetic acid (143.2 mg, 0.5 mmol) was dissolved in 5 ml of THF and oxalyl chloride (178.5 mg, 0.11 ml, 1.5 mmol), to which DMF was added. After reacting the mixture at room temperature for 1 hour, 3-amino-4-hydroxy-benzoic acid methyl ester (125.4 mg, 0.75 mmol) and pyridine (0.05 ml) were added thereto. The reaction mixture was reacted at room temperature. Upon completion of the reaction, the reaction mixture was extracted with ethylacetate and NaCl solution, thereafter the organic layer was dried over anhydrous MgSO$_4$, and concentrated. The residue was purified by silicagel column chromatography (N-Hexane: EtOAc:MeOH=6:3:1) to give the target compound as a white solid (183.2 mg, yield: 84.1%).

$^1$H-NMR (DMSO-d$_6$, 300 Hz) 11.10 (1H, s, OH), 9.24 (1H, s, NH), 8.69 (1H, m, aromatic-H), 7.60-7.64 (1H, m, aromatic-H), 7.30 (2H, d, J=8.4 Hz, aromatic-H), 6.94-6.99 (3H, m, aromatic-H), 4.74 (2H, s, CH$_2$), 3.79 (3H, s, CH$_3$), 2.04 (3H, m, adamantly-H), 1.83 (6H, m, adamantly-H), 1.72 (6H, m, adamantly-H)

Experimental Example 1

Inhibition of HIF-1 Mediated HRE Transcription Activity

To investigate the inhibition of HIF-1 transcription activity by the compound of the present invention, pGL3-basic vector (Promega) using luciferase as a reporter was cloned in multicloning site so as for HRE (Hypoxia Responsive Element, 5'-ACGTG-3') existing in human VEGF gene to be repeated 6 times, resulting in the construction of pGL3-HRE-luciferase vector.

The human rectal cancer cell line HCT116 was seeded in a 48-well cell culture vessel. On the next day, the cells were transfected with 25 ng of pGL3-HRE-luciferase vector and 2.5 ng of *Renilla* control vector by using Polyfect reagent. After culturing the cells for 24 hours, the medium was replaced, followed by further culture for 4 hours. Then, the cells were treated with the compound prepared in each example at the concentration of 10 μM respectively, followed by culture in hypoxic condition (oxygen 1%, nitrogen 94%, carbon dioxide 5%) for 12 hours. Lysate was obtained by using RIPA buffer, by which hypoxia-induced luciferase activity was measured by using dual-luciferase assay system (Promega). HIF-1 inhibition activity of the compound prepared in each example is shown in FIG. 1. Hypoxia-induced luciferase activity after the treatment of the compound prepared in example 1 or the compound prepared in comparative example 1 was measured by the same manner as described above except that the compound was treated at the concentrations of 0, 1, 3, 5, 10, and 20 μM. HIF-1 inhibition activity of each compound prepared in example 1 and comparative example 1 respectively was compared and the results are shown in Table 2 and FIG. 2.

TABLE 2

| | HRE transcription activity (%) | |
|---|---|---|
| | Compound of Example 1 | Compound of Comparative Example 1 |
| 0 μM | 100 | 100 |
| 1 μM | 57.7 | 119.4 |
| 3 μM | 32.1 | 121.5 |
| 5 μM | 25.4 | 98.8 |
| 10 μM | 23.0 | 75.6 |
| 20 μM | 19.8 | 43.1 |

FIG. 1 is a graph illustrating the HRE transcription activity affected by the treatment of the compound of an example of the present invention at the concentration of 10 μM.

FIG. 2 is a graph illustrating the inhibiting activity of the compound of an example of the present invention on HRE transcription.

As shown in Table 2, FIG. 1, and FIG. 2, the effect of each compound of the present invention on HRE transcription activity mediated by hypoxia-induced HIF-1 was examined. As a result, HRE activity was significantly inhibited by the compounds of the present invention. Particularly, compared with the compound of comparative example 1, the compound of example 1 (AC-428) demonstrated at least three times higher inhibition effect on HRE transcription activity in cancer cell line.

Therefore, it was confirmed that the compound of the present invention inhibits HRE transcription activity induced by HIF-1 to suppress cancer growth and metastasis, so that it can be effectively used as an active ingredient of an anticancer agent.

Experimental Example 2

Inhibition of HIF-1α Accumulation in Hypoxic Condition

HIF-1α protein is one of those proteins constructing HIF-1, which plays an important role in the expressions of HIF-1 target genes.

In this example, the compound of formula 1 that demonstrated strong inhibition effect on HIF-1 transcription activity in the above experimental example 1 was used to investigate the inhibition effect on HIF-1α accumulation in the rectal cancer cell line HCT116. Particularly, the inhibition effect of the compounds of the present invention prepared in the above examples on the production of HIF-1α induced in hypoxic condition was investigated by using Western blotting. The inhibition effect of the compound of formula 1 prepared in example 1 and the compound prepared in comparative example 1 on the production of HIF-1α induced in hypoxic condition was also investigated by using Western blotting.

The human colon cancer cell line HCT116 was seeded in cell culture vessel at the density of $2 \times 10^5$ cell/ml, followed by culture for 24 hours. The cells were pretreated in hypoxic condition (oxygen 1%; nitrogen 94%; carbon dioxide 5%; presented 1% $O_2$ in FIG. 1) for 4 hours to induce the accumulation of HIF-1α. The cells were treated with the compound of formula 1 dissolved in DMSO (0~30 μM), followed by culture for 12 hours in hypoxic condition. Then, nuclear extract was prepared by using RIPA buffer. To compare the expression of HIF-1 target gene according to hypoxic condition, the control group was examined in 20% oxygen condition. Approximately 30 μg of each nuclear extract sample proceeded to SDS PAGE (sodium dodecyl sulfate-polyacrylamide gel electrophoresis), which was transferred onto polyvinylidene fluoride membrane. The amount of HIF-1α protein was quantified by using HIF-1α antibody (R&D System) and HRP (horseradish peroxidase)-conjugated secondary antibody (Amersham-Pharmacia). GAPDH was used as the internal control gene.

To investigate whether or not the compounds of the present invention prepared in the above examples could affect the expression of the tumor suppressor VHL (Von Hippel-Lindau), VHL protein was treated thereto.

To confirm that the nuclear extract was equally contained on each PVDF membrane, HIF-1α antibody was eliminated from the membrane used for the detection of HIF-1α by using the buffer containing 2-mercaptoethanol and then β-actin was quantified. The results are shown in FIG. 3 and FIG. 4.

FIG. 3 is a diagram illustrating the inhibition of HIF-1α accumulation by the compounds of an example of the present invention.

Figure 4:
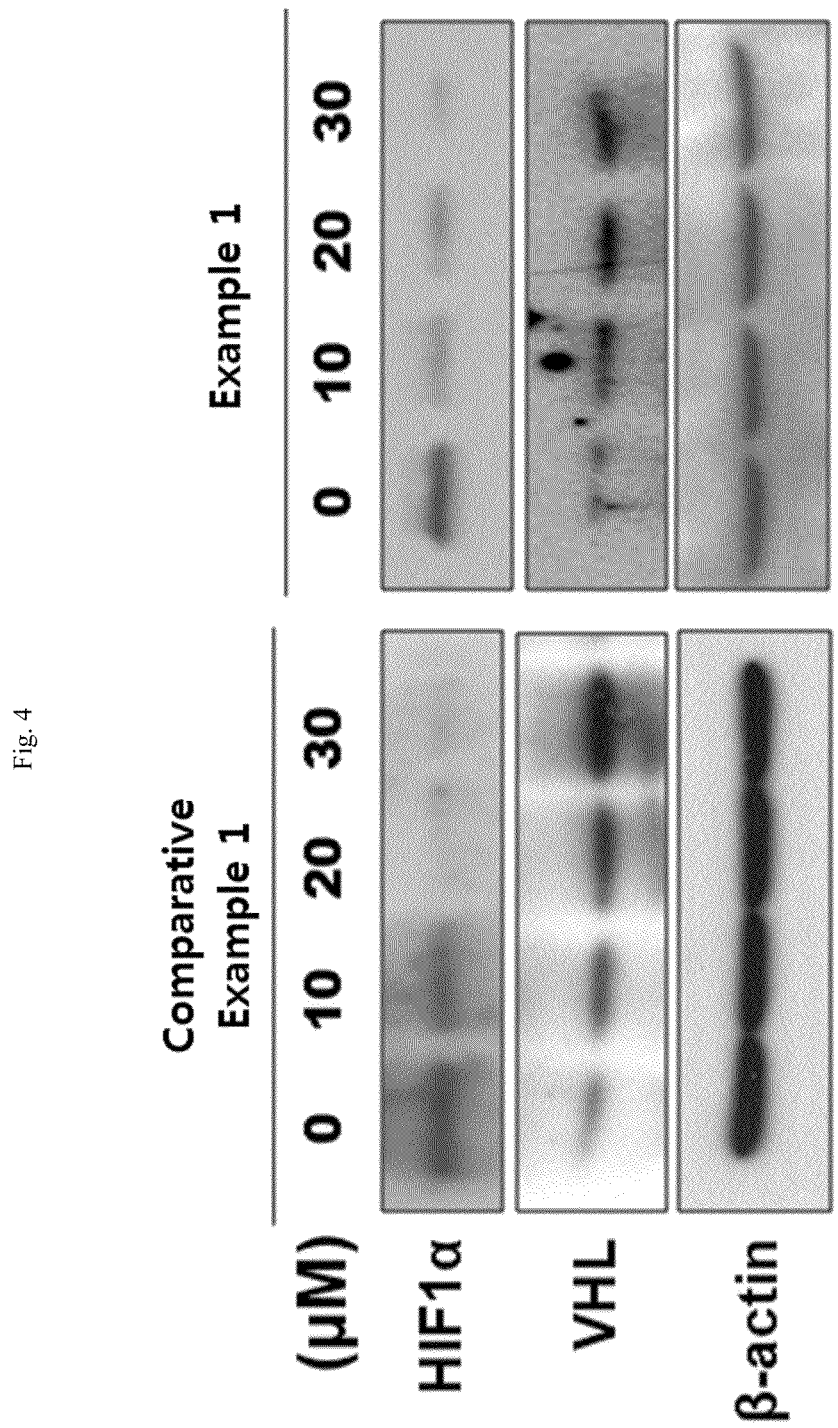
FIG. 4 is a diagram illustrating the inhibition of HIF-1α accumulation by the compound of an example of the present invention.

FIG. 4 is a diagram illustrating the inhibition of HIF-1α accumulation by the compound of an example of the present invention.

As shown in FIG. 3 and FIG. 4, the compound of the present invention did not change the generation of GAPDH or β-actin in hypoxic condition but inhibited the production of HIF-1α dose-dependently and increased the expression of the tumor suppressor VHL.

Therefore, it was confirmed that the compound of the present invention inhibits HIF-1α accumulation making cancer more malignant and at the same time increases the expression of the tumor suppressor VHL, so that it can be effectively used as an active ingredient of an anticancer agent.

Experimental Example 3

Effect of the Compound of Formula 1 on the Expressions of the HIF-1 Target Genes, VEGF and EPO (RT-PCR, Reverse Transcriptase Polymerase Chain Reaction)

Among the HIF-1 target genes, VEGF (vascular endothelial growth factor A) is an important angiogenesis factor playing a major role in cancer growth and metastasis, while EPO (erythropoietin) is a factor to accelerate the generation of erythrocytes. These target genes have been known to be involved in cancer growth and metastasis.

To investigate HIF-1 inhibition activity of the compound of the present invention, the inhibition of VEGF and EPO, two most representative HIF-1 target genes, by the compound of formula 1 prepared in example 1 was measured. Particularly, the colon cancer cell line HCT116 was used for the measurement as follows.

The human colon cancer cell line HCT116 was seeded in cell culture vessel at the density of $2 \times 10^5$ cell/ml, followed by culture for 24 hours. The cells were pretreated in hypoxic condition (oxygen 1%; nitrogen 94%; carbon dioxide 5%) for 4 hours to induce the accumulation of HIF-1α. The cells were treated with the compound of formula 1 prepared in example 1 at the concentrations of 0, 10, and 20 μM, followed by culture for 12 hours in hypoxic condition. Then, mRNA was extracted by using trizol. To compare the expression with that of HIF-1 target gene treated with the compound prepared in comparative example 1, the control was treated with the compound of comparative example 1 at the concentrations of 0, 10, 15, and 20 μM. From the extracted mRNA, cDNA was synthesized by using RT-PCR kit (Invitrogen). The amounts of mRNAs of the HIF-1α target genes VEGF (vascular endothelial growth factor A) and EPO (erythropoietin) were measured by using RT-PCR and real-time RT-PCR. As the internal control gene, GAPDH was amplified to measure the VEGF and EPO selective inhibition activity of the compound of formula 1. The results are shown in FIG. 5.

Figure 5:
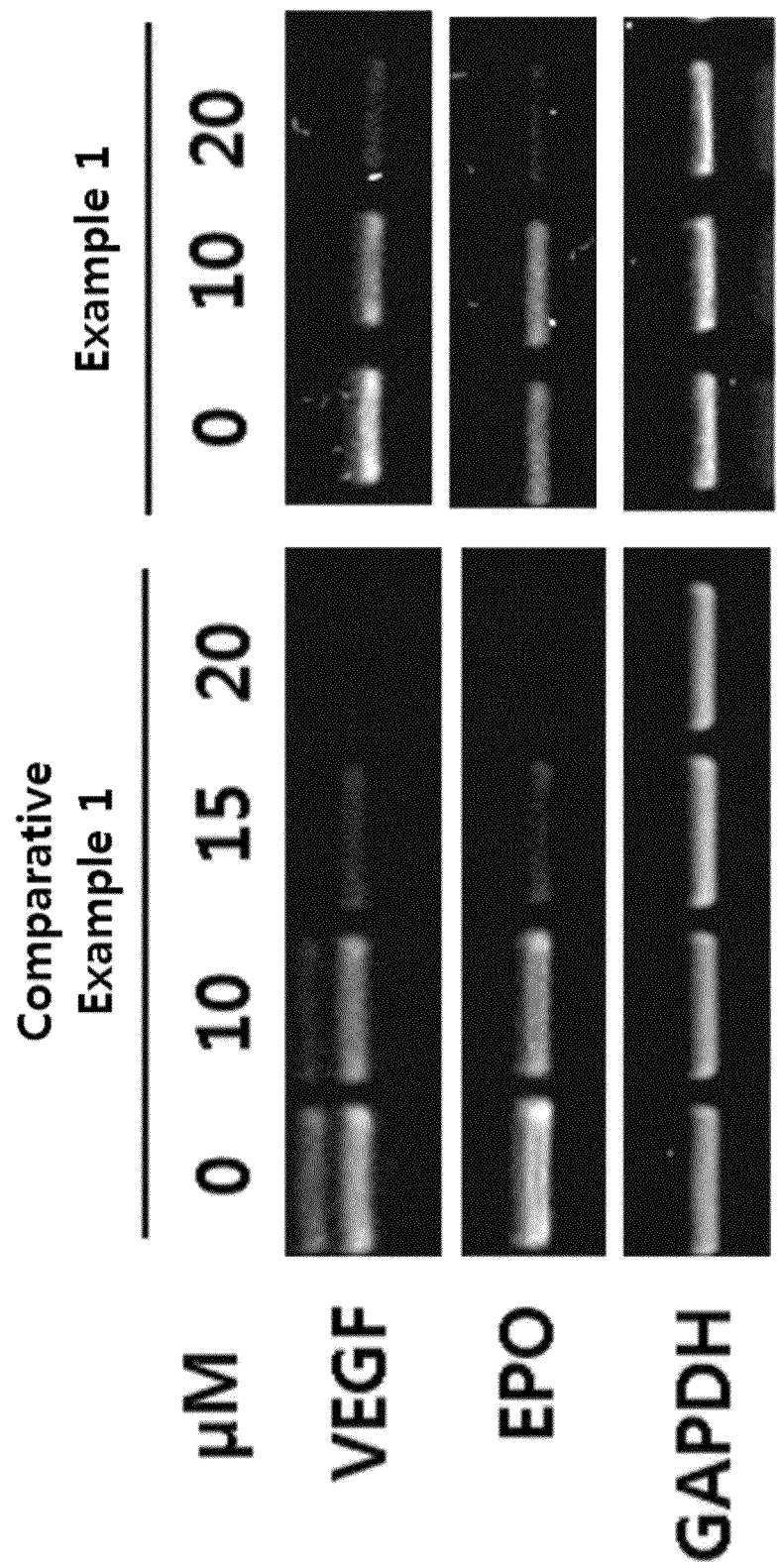
FIG. 5 is a diagram illustrating the inhibition of VEGF and EPO expressions by the compound of an example of the present invention.

FIG. 5 is a diagram illustrating the inhibition of VEGF and EPO expressions by the compound of an example of the present invention.

As shown in FIG. 5, the compound of formula 1 prepared in example 1 did not change the expression of GAPDH, the internal control gene, in hypoxic condition. However, the compound of example 1 inhibited the expressions of VEGF and EPO, the HIF-1 target genes, dose-dependently.

Therefore, it was confirmed that the compound of formula 1 of the present invention inhibits selectively the expressions of VEGF and EPO, the major factors playing an important role in cancer growth and metastasis, so that it can be effectively used as an active ingredient of an anticancer agent. Further, the compound of the present invention can also be effectively used as an active ingredient of a therapeutic agent for diabetic retinopathy and arthritis which are getting worse by the increase of hypoxia-induced VEGF expression.

Experimental Example 4

Measurement of In Vivo Anticancer Activity of the Compound Administered Via Intravenous Injection To evaluate the inhibition effect of the compound prepared in example 1 administered via intravenous injection on the growth of rectal cancer, in vivo anticancer activity in mouse was measured. Particularly, nude-mice were grouped for experimental and control groups (5 mice per group). Changes in body weight, tumor volume, and tumor weight were measured to evaluate in vivo anticancer activity.

Female nude mice at 6 weeks (BALB/c nu/nu, Charles River) were raised in a germ-free facility where temperature and humidity were maintained at proper levels during the whole experimental period. After anesthetizing each mouse, the human rectal cancer cell line HCT116 was transplanted in rectal tissues at the density of $4 \times 10^7$ cells/mouse, and then the opened rectum was sealed with surgical clips. After transplanting the rectal cancer cell line, the tumor volume was measured with calipers. When the tumor volume reached 54.5 mm$^3$, the compound of the present invention prepared in example 1 was treated thereto. Particularly, for the experimental group, the compound of example 1 was dissolved in the solvent composed of saline (80%), DMAC (10%), and tween 80 (10%), which is indicated as 'solvent A' hereinafter, at the concentration of 30 mg/kg. The prepared compound solution was intravenously administered to the experimental group mice once a day at the dose of 15 mg/kg. The control was treated with the solvent A only without the compound once a day via oral administration at the dose of 15 ml/kg. The comparative group was treated with the solvent A containing topotecan (2 mg/kg) via intravenous injection once a day at the dose of 15 ml/kg. The weight and the tumor volume were measured once a day on day 0, 2, 3, 4, 5, 6, and 8.

Tumor volume was calculated by the following mathematical formula 1. To investigate the toxicity according to the repeated intravenous administration of the compound of example 1, mouse weight changes were observed and presented in Table 3. Changes of tumor weight and volume are presented in Table 4. Inhibition rate (%) in Table 4 was calculated by the following mathematical formula 2, which indicates the inhibition of tumor growth by the compound presented by %.

Tumor Volume(mm$^3$)=(major axis length of tumor cells, mm)×(minor axis length of tumor cells, mm)$^2$×0.5  [Mathematical Formula 1]

Inhibition Rate (%)=[(Tumor Volume of Control−Tumor Volume of Experimental Group)/(Tumor Volume of Control)]×100  [Mathematical Formula 2]

TABLE 3

Mouse weight changes according to the repeated intravenous administration of the compound of example 1 (%)

| Group (n = 5) | Dose (mg/kg) | Day after the administration | | | | | | |
|---|---|---|---|---|---|---|---|---|
| | | 0 | 2 | 3 | 4 | 5 | 6 | 8 |
| Control group | 0 | 100.0 ± 0.0 | 103.2 ± 0.9 | 102.5 ± 0.9 | 102.0 ± 0.6 | 104.2 ± 3.3 | 106.6 ± 3.9 | 105.5 ± 4.6 |
| Comparative group | 2 | 100.0 ± 0.0 | 101.7 ± 1.0 | 101.8 ± 1.1 | 103.2 ± 5.4 | 99.1 ± 1.4 | 98.7 ± 1.7 | 95.6 ± 1.4 |
| Experimental group | 30 | 100.0 ± 0.0 | 96.5 ± 2.9 | 94.7 ± 2.3 | 96.0 ± 3.5 | 100.3 ± 1.5 | 101.4 ± 2.5 | 99.9 ± 2.3 |

As shown in Table 3, while the compound of example 1 was being intravenously administered repeatedly at the dose of 30 mg/kg, no specific symptom was observed. The body weight of the experimental group mouse on day 8 was not much different from that of the control, indicating there was no significant weight loss in the experimental group. Therefore, it was confirmed that the compound of formula 1 of the present invention has no toxicity, so that it can be used as an active ingredient of an anticancer agent.

TABLE 4

Tumor volume changes according to the repeated intravenous administration of the compound of formula 1 (mm$^3$)

| Group (n = 5) | Dose (mg/kg/ day) | Day after the administration ||||| 
|---|---|---|---|---|---|---|
| | | 0 | 2 | 4 | 6 | 8 |
| Control group | 0 | 0.0 ± 0.0 | 30.0 ± 5.3 | 105.7 ± 29.0 | 215.5 ± 52.8 | 325.7 ± 65.8 |
| Comparative group | 2 | 0.0 ± 0.0 | 16.5 ± 3.9 | 44.3 ± 10.1 | 69.1 ± 13.2 | 93.1 ± 22.3 |
| Inhibition rate (%) | | — | 44.9 | 58.1 | 67.9 | 71.4 |
| Experimental group | 30 | 0.0 ± 0.0 | 19.4 ± 5.8 | 50.6 ± 20.9 | 114.3 ± 36.8 | 176.8 ± 50.0 |
| Inhibition rate (%) | | — | 35.3 | 52.1 | 47.0 | 45.7 |

As shown in Table 4, in the experimental group treated with 30 mg/kg of the compound prepared in example 1, the growth of tumor was inhibited by 45.7%, compared with that in the control group.

Therefore, it was confirmed that the compound of the present invention has anticancer activity but hardly has toxicity when it is intravenously injected, so that it can be effectively used as an active ingredient of an anticancer agent.

Experimental Example 5

Measurement of In Vivo Anticancer Activity of the Compound Administered Via Intravenous Injection 2

To evaluate the inhibition effect of the compound prepared in example 1 administered via intravenous injection on the growth of kidney cancer, in vivo anticancer activity in mouse was measured. Particularly, nude-mice were grouped for experimental and control groups (5 mice per group). Changes in body weight, tumor volume, and tumor weight were measured to evaluate in vivo anticancer activity.

Female nude mice at 6 weeks (BALB/c nu/nu, Charles River) were raised in a germ-free facility where temperature and humidity were maintained at proper levels during the whole experimental period. After anesthetizing each mouse, the human kidney cancer cell line Caki-1 was transplanted in kidney tissues at the density of 4×10$^7$ cells/mouse, and then the opened kidney was sealed with surgical clips. After transplanting the kidney cancer cell line, the tumor volume was measured with calipers. When the tumor volume reached 52.7 mm$^3$, the compound of the present invention prepared in example 1 was treated thereto. Particularly, for the experimental group, the compound of example 1 was dissolved in the solvent composed of cremophor (10%), DMAC (10%), and pH 10 buffer (10%), which is indicated as 'solvent B' hereinafter, at the concentration of 20 mg/kg. The prepared compound solution was intravenously administered to the experimental group mice once a day at the dose of 15 mg/kg. The control was treated with the solvent B only without the compound once a day via oral administration at the dose of 15 ml/kg. The comparative group was treated with the solvent B containing topotecan (2 mg/kg) via intravenous injection once a day at the dose of 15 ml/kg. The weight and the tumor volume were measured once a day on day 0, 2, 4, 7, 9, 11, and 14.

Tumor volume was calculated by the mathematical formula 1 of Experimental Example 4. To investigate the toxicity according to the repeated intravenous administration of the compound of example 1, mouse weight changes were observed and presented in Table 5. Changes of tumor weight and volume are presented in Table 6. Inhibition rate (%) in Table 6 was calculated by the mathematical formula 2, which indicates the inhibition of tumor growth by the compound presented by %.

TABLE 5

Mouse weight changes according to the repeated intravenous administration of the compound of formula 1 (%)

| Group (n = 5) | Dose (mg/kg/ day) | Day after the administration |||||||
|---|---|---|---|---|---|---|---|---|
| | | 0 | 2 | 4 | 7 | 9 | 11 | 14 |
| Control group | 0 | 100.0 ± 0.0 | 103.5 ± 1.1 | 104.0 ± 1.6 | 104.9 ± 2.7 | 105.0 ± 2.7 | 105.4 ± 3.1 | 106.6 ± 5.4 |
| Experimental group | 20 | 100.0 ± 0.0 | 104.7 ± 1.7 | 105.3 ± 2.2 | 105.5 ± 3.1 | 106.6 ± 4.9 | 107.3 ± 6.8 | 109.5 ± 6.4 |
| Comparative group | 2 | 100.0 ± 0.0 | 104.7 ± 1.9 | 103.8 ± 3.8 | 103.4 ± 2.6 | 101.8 ± 3.6 | 103.0 ± 3.6 | 102.9 ± 5.3 |

As shown in Table 5, while the compound of example 1 was being intravenously administered repeatedly at the dose of 20 mg/kg, no specific symptom was observed. The Body weight of the experimental group mouse on the final day of observation (day 14) was not significantly reduced, compared with that of the control. Therefore, it was confirmed that the compound of formula 1 of the present invention hardly has toxicity, so that it can be used as an active ingredient of an anticancer agent.

TABLE 6

Tumor volume changes according to the repeated intravenous administration of the compound of example 1 and tumor weight of the final day

| Group (n = 5) | Dose (mg/kg/ day) | Tumor volume (mm³) | | | | | | | Tumor weight (mg) |
|---|---|---|---|---|---|---|---|---|---|
| | | Day after the administration | | | | | | | |
| | | 0 | 2 | 4 | 7 | 9 | 11 | 14 | 14 |
| Control group | 0 | 0.0 ± 0.0 | 20.9 ± 4.0 | 52.8 ± 11.9 | 102.3 ± 12.2 | 148.9 ± 30.4 | 204.5 ± 39.2 | 289.7 ± 64.5 | 909.3 ± 216.0 |
| Experimental group | 20 | 0.0 ± 0.0 | 17.1 ± 2.0 | 41.4 ± 13.5 | 77.6 ± 11.8 | 107.0 ± 18.5 | 141.9 ± 14.8 | 200.2 ± 34.2 | 640.0 ± 61.8 |
| Inhibition rate (%) | | — | 18.4 | 21.6 | 24.2 | 28.2 | 30.6 | 30.9 | 29.6 |
| Comparative group | 2 | 0.0 ± 0.0 | 16.7 ± 2.3 | 38.7 ± 4.8 | 67.8 ± 8.6 | 88.5 ± 19.6 | 120.9 ± 36.0 | 156.9 ± 51.3 | 472.4 ± 137.6 |
| Inhibition rate (%) | | — | 20.1 | 26.6 | 33.8 | 40.6 | 40.9 | 45.8 | 48.0 |

As shown in Table 6, in the experimental group treated with 20 mg/kg of the compound prepared in example 1, the growth of tumor was inhibited by 30%, compared with that in the control group.

In addition, to investigate whether or not the anticancer activity shown in experimental example 5 was attributed to the decrease of HIF-1α expression, tumor tissue immune response experiment was performed. The results are shown in FIG. 6.

Figure 6:
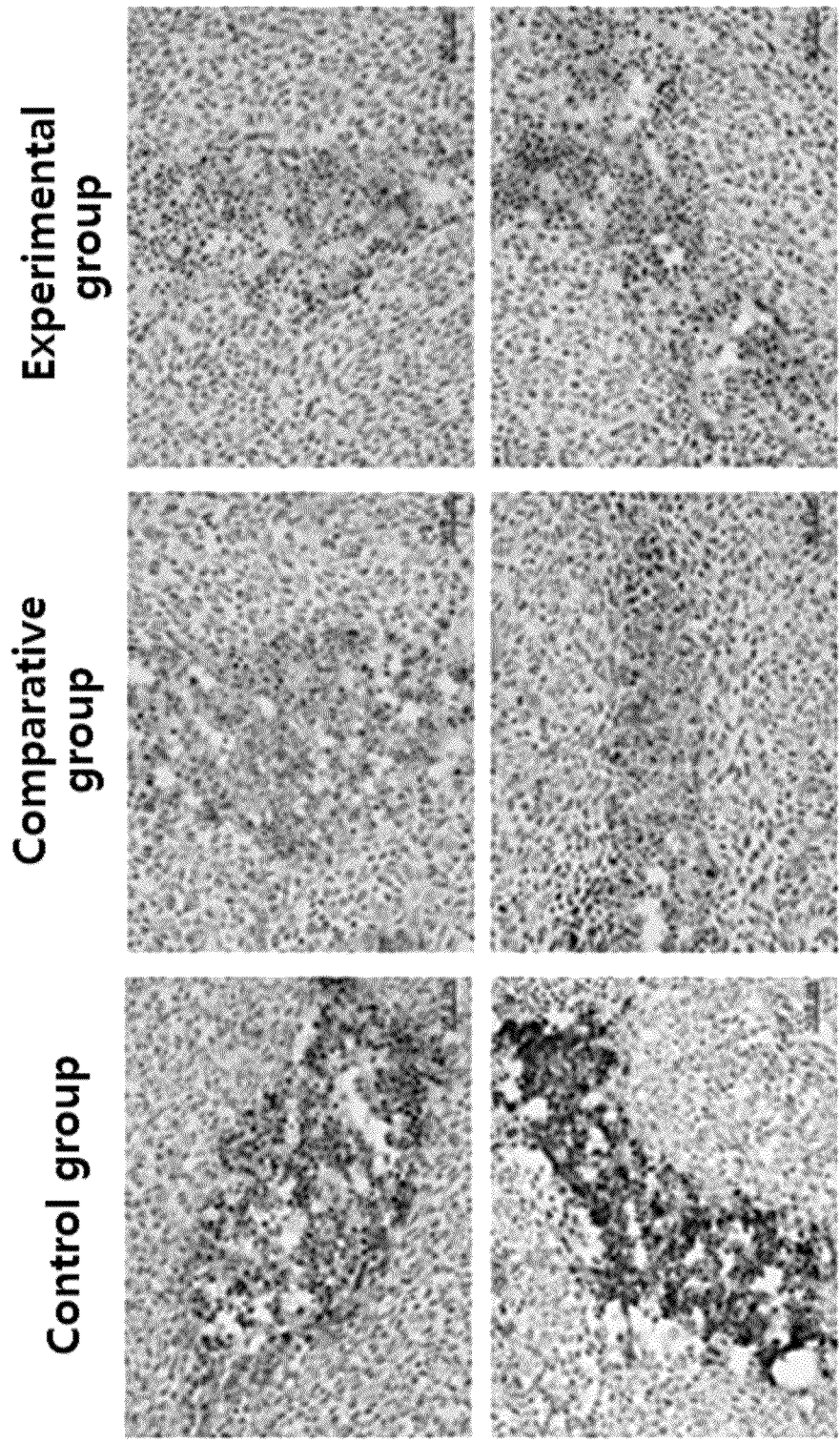
FIG. 6 is a diagram illustrating the inhibition of HIF-1α expression by the compound of an example of the present invention observed under optical microscope.

FIG. 6 is a diagram illustrating the inhibition of HIF-1α expression by the compound of an example of the present invention observed under optical microscope.

As shown in FIG. 6, HIF-1α expression was very peculiar in the control group, while HIF-1α expression was significantly reduced in tumor tissue of the experimental group mouse treated with the compound of example 1.

Therefore, it was confirmed that the compound of the present invention inhibits HIF-1α expression and thus has anticancer activity when it is intravenously injected but hardly has toxicity, so that it can be effectively used as an active ingredient of an anticancer agent.

Experimental Example 6

Angiogenesis Inhibition Activity

The following experiment was performed to investigate if the compound of formula 1 could inhibit angiogenesis along with the tumor growth.

Particularly, the experimental group composed of 5 female mice (C57BL) at 6 weeks was transplanted with B16F10 melanoma cell line. After the cancer cells were grown, the mice were treated with the compound of formula 1 via intraperitoneal injection at the dose of mg/kg every day for 5 days. Inhibition of angiogenesis and the tumor growth were observed. In the meantime, the control group was treated with the mixed solution comprising 10% DMAC, 10% cremophor and 80% buffer (pH 10) every day. The comparative group was treated with topotecan at the dose of 2 mg/kg once every other day. Weight changes and the newly generated blood vessels were measured and the results are shown in Table 7, Table 8, FIG. 7, and FIG. 8. The tumor volume shown in Table 8 was calculated by the mathematical formula 1 of experimental example 4 and the inhibition rate was calculated by the mathematical formula 2 of experimental example 4.

TABLE 7

Mouse weight changes according to the intraperitoneal administration of the compound of example 1 (%)

| Group (n = 5) | Dose (mg/kg) | Day after the administration | | |
|---|---|---|---|---|
| | | 0 | 2 | 5 |
| Control group | 0/day | 100.0 ± 0.0 | 102.9 ± 0.7 | 107.5 ± 1.7 |
| Experimental group | 20/day | 100.0 ± 0.0 | 102.6 ± 1.6 | 107.6 ± 3.9 |
| Comparative group | 2/2 day | 100.0 ± 0.0 | 101.2 ± 0.6 | 103.7 ± 1.4 |

As shown in Table 7, while the compound of example 1 was being administered via intraperitoneal injection repeatedly at the dose of 20 mg/kg, no specific symptom was observed. The Body weight of the experimental group mouse on the final day of observation (day 5) was not significantly reduced, compared with that of the control. Therefore, it was confirmed that the compound of formula 1 of the present invention hardly has toxicity, so that it can be used as an active ingredient of an anticancer agent.

TABLE 8

Tumor volume changes according to the repeated intraperitoneal administration of the compound of formula 1 (mm³)

| Group (n = 5) | Dose (mg/kg) | Day after the administration | | | |
|---|---|---|---|---|---|
| | | 0 | 3 | 4 | 5 |
| Control group | 0/day | 0.0 ± 0.0 | 33.4 ± 6.4 | 47.0 ± 7.8 | 78.5 ± 11.2 |
| Experimental group | 20/day | 0.0 ± 0.0 | 26.8 ± 3.6 | 36.4 ± 4.8 | 55.8 ± 5.8 |
| Inhibition rate (%) | | — | 19.7 | 22.5 | 28.9 |
| Comparative group | 2/2 day | 0.0 ± 0.0 | 20.9 ± 2.6 | 27.1 ± 2.3 | 42.9 ± 4.5 |

TABLE 8-continued

Tumor volume changes according to the repeated intraperitoneal administration of the compound of formula 1 (mm³)

| Group (n = 5) | Dose (mg/kg) | Day after the administration | | | |
|---|---|---|---|---|---|
| | | 0 | 3 | 4 | 5 |
| group Inhibition rate (%) | | — | 37.4 | 42.4 | 45.4 |

As shown in Table 8, in the experimental group treated with 20 mg/kg of the compound prepared in example 1, the growth of tumor was inhibited by 28.9%, compared with that in the control group.

Figure 7:
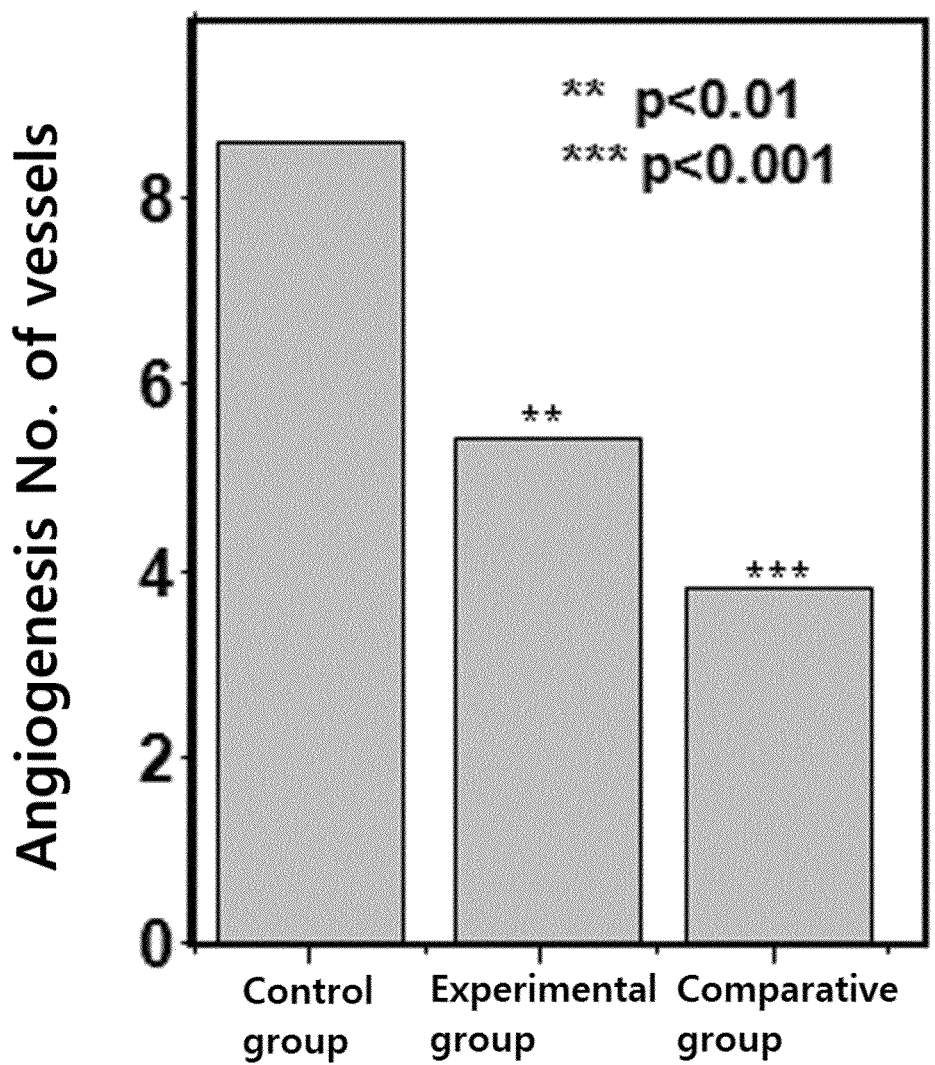
FIG. 7 is a graph illustrating the effect of the compound of an example of the present invention on angiogenesis.

FIG. 7 is a graph illustrating the effect of the compound of an example of the present invention on angiogenesis.

FIG. 8 is a photograph illustrating the effect of the compound of an example of the present invention on angiogenesis.

As shown in FIG. 7 and FIG. 8, when the compound of example 1 was treated to tumor tissue, angiogenesis was reduced approximately by 40%, compared with non-treated group.

Therefore, it was confirmed that the compound of formula 1 of the present invention has angiogenesis inhibition activity, so that it can be used as an active ingredient of an anticancer agent.

Experimental Example 7

Cell Migration Inhibition Activity

To evaluate cell migration inhibition effect of the compound of example 1, wound-healing experiment was performed. Particularly, an insert (Ibidi) was placed in the center of a 6-well cell culture dish and HCT116 cells (3×10⁵ cell/ml) were loaded in each well by 70 μl. Medium was filled in around the insert. 24 hours later, the insert was carefully eliminated by using forceps, and the cells were washed with medium carefully not to be detached from the bottom of the culture dish. The control group was added with the diluted medium supplemented with DMSO. The experimental group was added with the diluted medium supplemented with 10 μM of the compound of example 1. 48 hours later, cell migration in each group was observed. The results are shown in FIG. 9.

Figure 9:
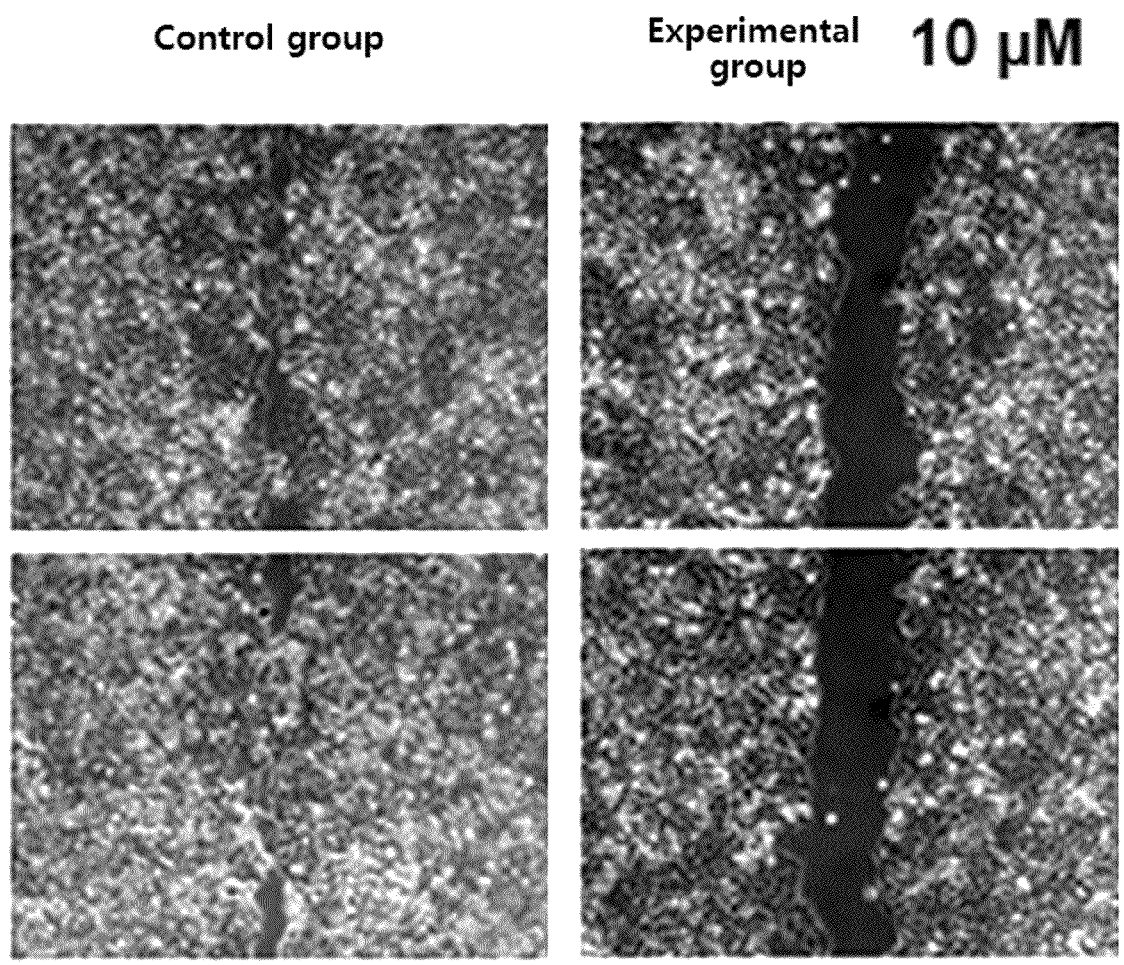
FIG. 9 is a photomicrograph illustrating the inhibition of cell migration by the compound of an example of the present invention.

FIG. 9 is a photomicrograph illustrating the inhibition of cell migration by the compound of an example of the present invention.

As shown in FIG. 9, the group treated with 10 μM of the compound of example 1 demonstrated significantly reduced cell migration.

Therefore, it was confirmed that the compound of the present invention has cell migration inhibition activity, so that it can be effectively used as an active ingredient of an anticancer agent.

Experimental Example 8

Cancer Metastasis Inhibition Activity

The following experiment was performed to confirm the inhibition effect of the compound of example 1 on cancer metastasis.

Particularly, the experimental group composed of 6 female mice (C57BL) at 6 weeks was transplanted with B16F10 melanoma cell line. After the cancer cells were grown, the mice were treated with the compound of formula 1 via intraperitoneal injection at the dose of mg/kg every day for 12 days. Inhibition of angiogenesis and the tumor growth were observed. In the meantime, the control group was treated with purified water every day. The comparative group was treated with topotecan at the dose of 2 mg/kg once every other day. Weight changes and cancer metastasis were measured and the results are shown in Table 9, Table 10, and FIG. 10.

TABLE 9

Mouse weight changes according to the intraperitoneal administration of the compound of example 1 (%)

| Group (n = 6) | Dose (mg/kg) | Day after the administration | | | | | |
|---|---|---|---|---|---|---|---|
| | | 0 | 2 | 5 | 7 | 9 | 12 |
| Control group | 0/day | 100.0 ± 0.0 | 101.4 ± 2.5 | 105.5 ± 2.9 | 105.0 ± 2.5 | 106.8 ± 2.6 | 107.1 ± 2.7 |
| Experimental group | 20/day | 100.0 ± 0.0 | 98.7 ± 3.4 | 101.2 ± 4.6 | 103.4 ± 3.8 | 107.6 ± 2.8 | 107.6 ± 3.3 |
| Comparative group | 2/2 day | 100.0 ± 0.0 | 101.0 ± 2.9 | 103.5 ± 6.1 | 104.0 ± 4.6 | 104.3 ± 6.2 | 103.7 ± 5.5 |

As shown in Table 9, while the compound of example 1 was being administered via intraperitoneal injection repeatedly at the dose of 20 mg/kg, no specific symptom was observed. The Body weight of the experimental group mouse on the final day of observation (day 12) was not significantly reduced, compared with that of the control. Therefore, it was confirmed that the compound of formula 1 of the present invention hardly has toxicity, so that it can be used as an active ingredient of an anticancer agent.

TABLE 10

Changes of metastasis colony number according to the intraperitoneal administration of the compound of example 1

| Group (n = 6) | Dose (mg/kg) | Metastasis colony number |
|---|---|---|
| Control group | 0 | 306.8 ± 23.1 |
| Experimental group | 20/day | 207.0 ± 47.5 |
| Metastasis inhibition rate (%) | — | 32.5 |
| Comparative group | 2/2 day | 148.3 ± 49.4 |
| Metastasis inhibition rate (%) | — | 51.7 |

Figure 10:
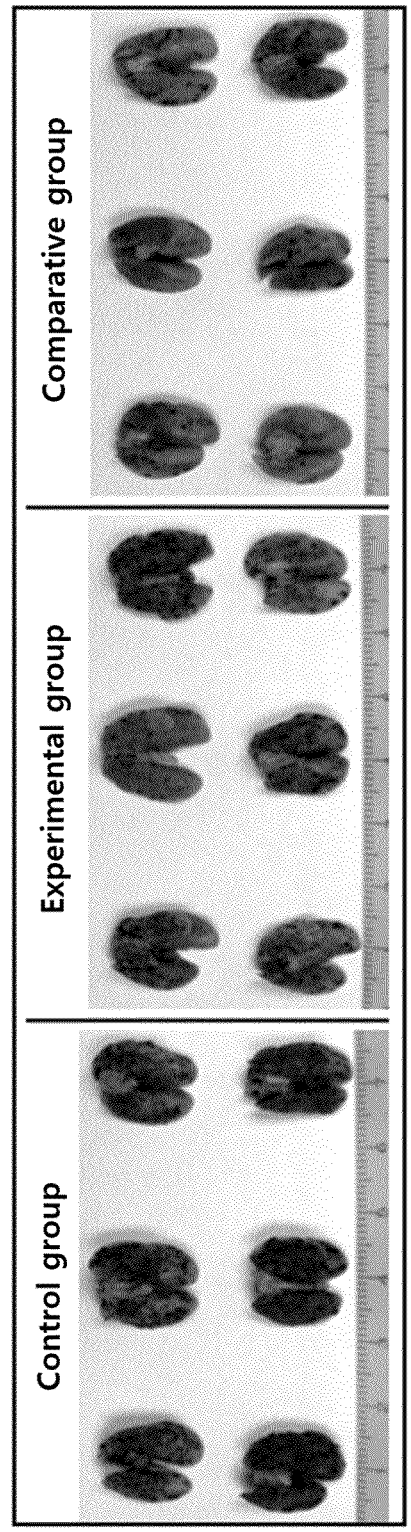
FIG. 10 is a photograph illustrating the changes of metastasis colony number in lung by the treatment of the compound of an example of the present invention.

FIG. 10 is a photograph illustrating the changes of metastasis colony number in lung by the treatment of the compound of an example of the present invention.

As shown in Table 10 and FIG. 10, the mice were sacrificed on the last day of experiment (day 12) and then cancer colonies in lung were counted by the naked eye. As a result, 306.8 metastasis colonies at average were observed in the control group, while 207 colonies were observed in the experimental group treated with the compound of example 1 at the dose of 20 mg/kg, indicating the compound of the present invention showed significant metastasis inhibition effect up to 32.5%.

Therefore, it was confirmed that the compound of formula 1 of the present invention has metastasis inhibition activity, so that it can be used as an active ingredient of an anticancer agent.

The Manufacturing Examples of the composition for the present invention are described hereinafter.

Manufacturing Example 1

Preparation of Powders

| Compound of formula 1 | 2 g |
|---|---|
| Lactose | 1 g |

Powders were prepared by mixing all the above components, which were filled in airtight packs according to the conventional method for preparing powders.

Manufacturing Example 2

Preparation of Tablets

| Compound of formula 1 | 100 mg |
|---|---|
| Corn starch | 100 mg |
| Lactose | 100 mg |
| Magnesium stearate | 2 mg |

Tablets were prepared by mixing all the above components by the conventional method for preparing tablets.

Manufacturing Example 3

Preparation of Capsules

| Compound of formula 1 | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 3

Preparation of Injectable Solutions

| Compound of formula 1 | 10 µg/ml |
|---|---|

-continued

| Weak HCl BP | until pH 3.5 |
|---|---|
| Injectable NaCl BP | up to 1 ml |

The compound of formula 1 of the present invention was dissolved in proper volume of injectable NaCl BP. pH of the prepared solution was regulated as 3.5 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A compound represented by the following formula 1 or a pharmaceutically acceptable salt thereof:

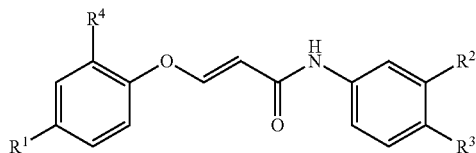

[Formula 1]

(In the formula 1,
$R^1$ is $C_{1-10}$ straight or branched alkyl, or $C_{8-12}$ bicyclic ring,
$R^2$ is —H, $COOR_5$, $COOR_5R_6$, —$SO_2NH_2$, —$SO_2$—($C_{1-4}$ straight or branched alkyl), or —$CONHR_7$,
$R^3$ is —H, —OH, or —COO—($C_{1-4}$ straight or branched alkyl),
$R^4$ is —H, or $C_{1-4}$ straight or branched alkyl,
$R^5$ is —H, $C_{1-4}$ straight or branched alkyl, or $C_{1-4}$ alkoxy,
$R^6$ is —$NH_2$, or 5-6 membered heterocycle containing one or more N or O,
$R^7$ is —H, or —$(CH_2)_n$—$R^8$,
$R^8$ is —H, 5-6 membered heteroaryl containing one or more N or O, or 5-6 membered heterocycle containing one or more N or O, and
n is an integer of 0-4).

2. The compound or the pharmaceutically acceptable salt thereof according to claim 1, wherein the $R^1$ is $C_{1-10}$ straight or branched alkyl, or

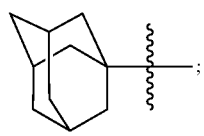 [SMILES: *C12CC3CC(CC(C3)C1)C2]

$R^2$ is —H, $COOR_5$, $COOR_5R_6$, —$SO_2NH_2$, —$SO_2CH_3$, or —$CONHR_7$;
$R^3$ is —H, —OH, or $COOCH_3$;
$R^4$ is —H, or methyl;
$R^5$ is —H, methyl, ethyl, methoxy, or ethoxy;

R⁶ is —NH₂, or 5-6 membered heterocycle containing one or more N or O;
R⁷ is —H, or —(CH₂)ₙ—R⁸;
R⁸ is —H, 5-6 membered heteroaryl containing one or more N or O, or 6 membered heterocycle containing one or more N or O;
n is an integer of 0-3.

3. The compound or the pharmaceutically acceptable salt thereof according to claim 1, wherein the R¹ is

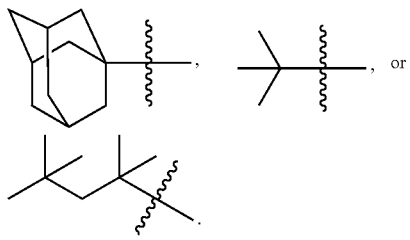

4. The compound or the pharmaceutically acceptable salt thereof according to claim 1, wherein the R² is —H, —COOH, —COOCH₃, —COOCH₂CH₃, —COOCH₂CH₂OCH₃, —CONH₂, SO₂NH₂, —SO₂CH₃,

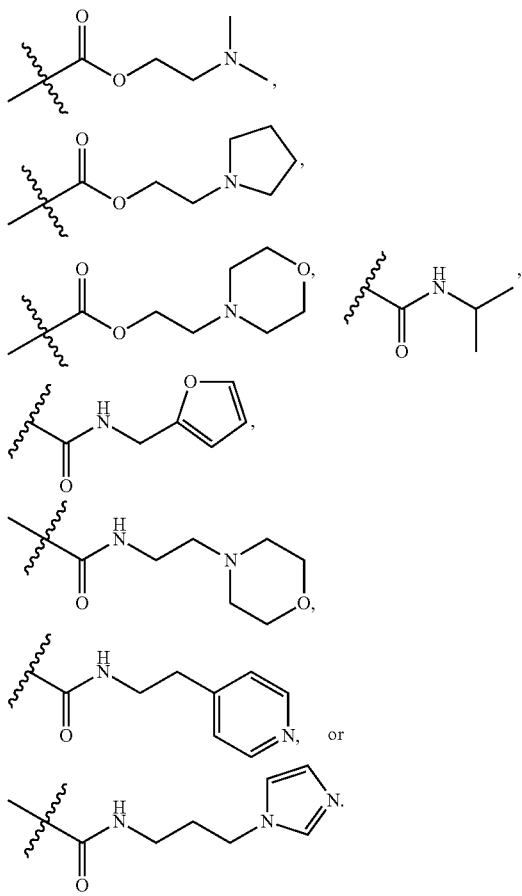

5. The compound or the pharmaceutically acceptable salt thereof according to claim 1, wherein the compound represented by formula 1 is selected from the group consisting of
(E)-3-[3-(4-adamantan-1-yl-phenoxy)-acryloylamino]-benzoic acid methylester,
(E)-3-(3-(4-t-butylphenoxy)acrylamido)benzoic acid methylester,
(E)-3-(3-(4-(2,4,4-trimethylpentan-2-yl)phenoxy)acrylamido)benzoic acid methylester,
(E)-3-(3-(4-adamantan-1-yl-2-methylphenoxy) acrylamido)benzoic acid methylester,
(E)-4-(3-(4-adamantan-1-yl-phenoxy)acrylamido)benzoic acid methylester,
(E)-3-(4-adamantan-1-yl-phenoxy)-N-(3-sulfamoylphenyl) acrylamide,
(E)-3-(4-adamantan-1-ylphenoxy)-N-(3-(methylsulfonyl)phenyl)acrylamide,
(E)-5-[3-(4-adamantan-1-yl-phenoxy)-acryloamino]-2-hydroxy-benzoic acid methylester,
(E)-3-[3-(4-adamantan-1-yl-phenoxy)-acryloylamino]-benzoic acid,
(E)-3-(3-(4-adamantan-1-yl-phenoxy)acrylamido)benzoic acid ethylester,
(E)-3-(3-(4-adamantan-1-ylphenoxy)acrylamido)benzoic acid 2-methoxyethylester,
(E)-3-(3-(4-adamantan-1-yl-phenoxy)acrylamido)benzoic acid 2-(dimethylamino)ethylester,
(E)-3-(3-(4-adamantan-1-yl-phenoxy)acrylamido)benzoic acid 2-pyrrolidine-1-yl)ethylester,
(E)-3-(3-(4-adamantan-1-yl-phenoxy)acrylamido)benzoic acid morpholinoethylester,
(E)-3-[3-(4-adamantan-1-yl-phenoxy)-acryloylamino]-benzamide,
(E)-3-[3-(4-adamantan-1-yl-phenoxy)-acryloylamino]-N-isopropyl-benzamide,
(E)-3-[3-(4-adamantan-1-yl-phenoxy)-acryloylamino]-N-furan-2-ylmethyl-benzamide,
(E)-3-[3-(4-adamantan-1-yl-phenoxy)-acryloylamino]-N-(2-morpholine-4-yl-ethyl)-benzamide,
(E)-3-[3-(4-adamantan-1-yl-phenoxy)-acryloylamino]-N-(2-pyridine-4-yl-ethyl)-benzamide,
(E)-3-[3-(4-adamantan-1-yl-phenoxy)-acryloylamino]-N-(3-imidazole-1-yl-propyl)-benzamide,
(E)-3-(3-(4-(2,4,4-trimethylpentan-2-yl)phenoxy)acrylamido)benzoic acid,
(E)-2-methoxyethyl 3-(3-(4-(2,4,4-trimethylpentan-2-yl)phenoxy)acrylamido)benzoate, and
(E)-2-morpholinoethyl 3-(3-(4-(2,4,4-trimethylpentan-2-yl)phenoxy)acrylamido)benzoate.

6. A preparation method of the compound of formula 1, as shown in the following reaction formula 1, comprising the following step: Hunig base and condensation reagent are added to the compound represented by formula 2 and the compound represented by formula 3, used as starting materials to induce reaction, in the presence of an organic solvent to give the compound represented by formula 1:

[Reaction Formula 1]

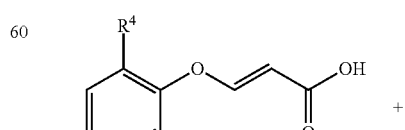

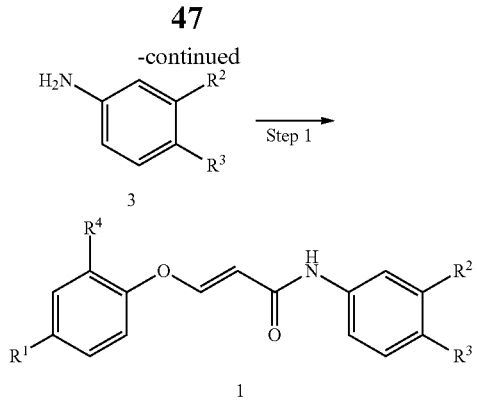

(In reaction formula 1, $R^1$, $R^2$, $R^3$ and $R^4$ are as defined in formula 1).

7. The preparation method of the compound of formula 1 according to claim 6, wherein the Hunig base is diisopropylamine (DIPEA) or triethylamine (TEA).

8. The preparation method of the compound of formula 1 according to claim 6, wherein the condensation reagent is one or more reagents selected from the group consisting of O-(7-azabenzotriazol-1-yl)-N,N,N',N'-tetramethyl-uronium-tetrafluoroborate (HATU), 1-[3-(dimethylamino)propyl]-3-ethylcarbodiimide hydrochloride (EDC), O-benzotriazol-N,N,N',N'-tetramethyl-uronium-hexafluoro-phosphate (HBTU), 1-hydroxybenzotriazole (HOBt), benzotriazol-1-yl-oxy-tris-pyrrolidino-phosphoniumhexafluoro phosphate (PyBOP), and 1-hydroxy-7-azabenzo triazole.

9. The preparation method of the compound of formula 1 according to claim 6, wherein the organic solvent is dimethylformamide (DMF) or methylenechloride ($CH_2Cl_2$).

10. A pharmaceutical composition for the prevention or treatment of cancer comprising the compound of claim 1 as an active ingredient.

11. The pharmaceutical composition according to claim 10, wherein the cancer is selected from the group consisting of solid cancers generally caused by the accumulation of HIF-1α such as colorectal cancer, liver cancer, stomach cancer, breast cancer, colon cancer, bone cancer, pancreatic cancer, head or neck cancer, uterine cancer, ovarian cancer, rectal cancer, esophageal cancer, small bowel neoplasm, anal cancer, colon cancer, carcinoma of the fallopian tubes, endometrial carcinoma, cervical carcinoma, vaginal carcinoma, vulva carcinoma, Hodgkin's disease, prostate cancer, bladder cancer, kidney cancer, ureter cancer, renal cell carcinoma, kidney pelvic carcinoma, and CNS tumors.

12. The pharmaceutical composition according to claim 10, wherein the composition demonstrated anticancer activity by inhibiting HIF-1 activity.

13. A pharmaceutical composition for the prevention or treatment of diabetic retinopathy comprising the compound of claim 1 as an active ingredient.

14. The pharmaceutical composition according to claim 13, wherein the composition inhibits angiogenesis by suppressing HIF-1 activity and VEGF protein expression.

15. A pharmaceutical composition for the prevention or treatment of rheumatoid arthritis comprising the compound of claim 1 as an active ingredient.

16. The pharmaceutical composition according to claim 15, wherein the composition inhibits angiogenesis by suppressing HIF-1 activity.

17. A method for treating cancer containing the step of administering a therapeutically effective dose of the compound represented by formula 1 or the pharmaceutically acceptable salt thereof of claim 1 to a patient having cancer in need of treatment.

18. A method for treating diabetic retinopathy containing the step of administering a therapeutically effective dose of the compound represented by formula 1 or the pharmaceutically acceptable salt thereof of claim 1 to a patient having diabetic retinopathy in need of treatment.

19. A method for treating rheumatoid arthritis containing the step of administering a therapeutically effective dose of the novel compound represented by formula 1 or the pharmaceutically acceptable salt thereof of claim 1 to a patient having rheumatoid arthritis in need of treatment.

* * * * *